(12) United States Patent
Inokuchi et al.

(10) Patent No.: US 7,337,186 B2
(45) Date of Patent: Feb. 26, 2008

(54) CLASSIFICATION FACTOR DETECTION

(75) Inventors: Akihiro Inokuchi, Yokohama (JP); Hisashi Kashima, Yamato (JP)

(73) Assignee: International Business Machines Corporation, Armonk, NY (US)

( * ) Notice: Subject to any disclaimer, the term of this patent is extended or adjusted under 35 U.S.C. 154(b) by 494 days.

(21) Appl. No.: 10/890,419

(22) Filed: Jul. 13, 2004

(65) Prior Publication Data

US 2005/0021554 A1 Jan. 27, 2005

(30) Foreign Application Priority Data

Jul. 23, 2003 (JP) ............................. 2003-278138

(51) Int. Cl.
G06F 7/00 (2006.01)
G06F 17/30 (2006.01)

(52) U.S. Cl. .......................................... 707/102; 707/6

(58) Field of Classification Search ................ 707/102, 707/6
See application file for complete search history.

(56) References Cited

U.S. PATENT DOCUMENTS

| | | | | |
|---|---|---|---|---|
| 5,539,838 | A * | 7/1996 | Shimura | 382/128 |
| 6,108,435 | A * | 8/2000 | Mori et al. | 382/106 |
| 6,606,659 | B1 * | 8/2003 | Hegli et al. | 709/225 |
| 2004/0110172 | A1 * | 6/2004 | Olson et al. | 435/6 |

OTHER PUBLICATIONS

Alberts et al. "Essential Cell Biology."
Asai et al. "Efficient Substructure Discovery From Large Semi-Structured Data," Technical Report from Data Engineering Technical Group in the Institute of Electronics, Information and Communication Engineers, vol. 101, No. 342, 1-8.
Cook et al. "Substructure Discovery Using Minimum Description Length and Backround Knowledge," Journal of Artificial Intelligence Research, vol. 1, pp. 231-255, 1994.

(Continued)

Primary Examiner—Mohammad Ali
Assistant Examiner—Van H Ngo
(74) Attorney, Agent, or Firm—Scully, Scott, Murphy & Presser, P.C.; Lisa Yamonaco

(57) ABSTRACT

Detects a condition for classification of data. Apparatus detects a set of some constituents as a factor of the classification. Apparatus has means for selecting a pattern which is a set of constituents; means of selecting a second pattern formed of the first pattern and at least one constituent added to the first pattern; means of generating an evaluation value for a measure of classification of the plurality of objects under a condition including the first pattern but not the second pattern on the basis of the number of objects satisfying the classification condition in the plurality of objects classified into the first group and the number of objects satisfying the classification condition in the objects classified into the second group; and means of outputting the first and second patterns as a factor of classification when the measure indicated by the evaluation value exceeds a reference measure.

14 Claims, 15 Drawing Sheets

OTHER PUBLICATIONS

Dehaspe et al. "Finding Frequent Substructures in the Chemical Compounds," Proc. Of thr 4th KDD, pp. 30-36.

Readt et al. "The Levelwise Version Space Algorithm and its Application to Molecular Fragment Finding," Proc. of the 17th IJCAI, pp. 853-859.

Inokuchi et al. "An Apriori-Based Algorithm for Mining Frequent Substructures From Graph Data," Proc. of the 4th PKDD, pp. 12-23.

Inokuchi et al. "A Fast Algorithm for Mining Frequent Connected Subgraphs," IBM Research Report, RTO448, Feb. 2002.

Inokuchi et al. "Data Mining in HIV Data," The 58th Special Interest Group on Knowledge Base System, 2002.

Kramer et al. "Molecular Feature Mining in HIV Data," Proc. of the 17th International Conference on Knowledge Discovery and Data Mining, pp. 136-143.

Kuramochi et al. "Frequent Subgraph Discovery," Procs. of the 1st ICDM.

Kuramochi et al. "Discoverin Frequent Geometric Subgraphs," Technical Report 02-024, 2002.

Matsuda et al. "Extension of Graph-Based Induction for General Graph Structured Data," Proc. of the 4th PAKDD, pp. 420-431.

Matsuzawa et al. "Mining Structured Association Patterns From Databases," Proc. of the 4th Pacific-Asia Conference on Knowledge Discovery and Data Mining.

Morimoto. "Spatial Data Mining Algorithm for Enumerating Frequent Neighboring Class Set," The 2nd Data Mining Workshop, pp. 1-10.

Morishita et al. "Traversing Itemset Lattices With Statistical Metric Pruning," Proc. Of POS 2000.

Motoda, "Machine Learning Techniques to Make Computers Easier to Use," Proc. of the 15th IJCAI, vo. 2, pp. 1622-1631.

Wang et al. Automated Discovery of Active Motifs in Three Dimensional Molecules, Proc. of the 3rd International Conference on KDD, pp. 89-95, 1997.

Wang et al. "Finding Patterns in Three-Dimensional Graphs: Algorithms and Applications to Scientic Data Mining," IEEE Transactions on Knowledge and Engineering, vol. 14, No. 4, pp. 731-749, 2002.

Zaki. "Efficiently Mining Frequent Trees in a Forest," Proc. of the 8th International Conference on KDD.

* cited by examiner

[Figure 1]
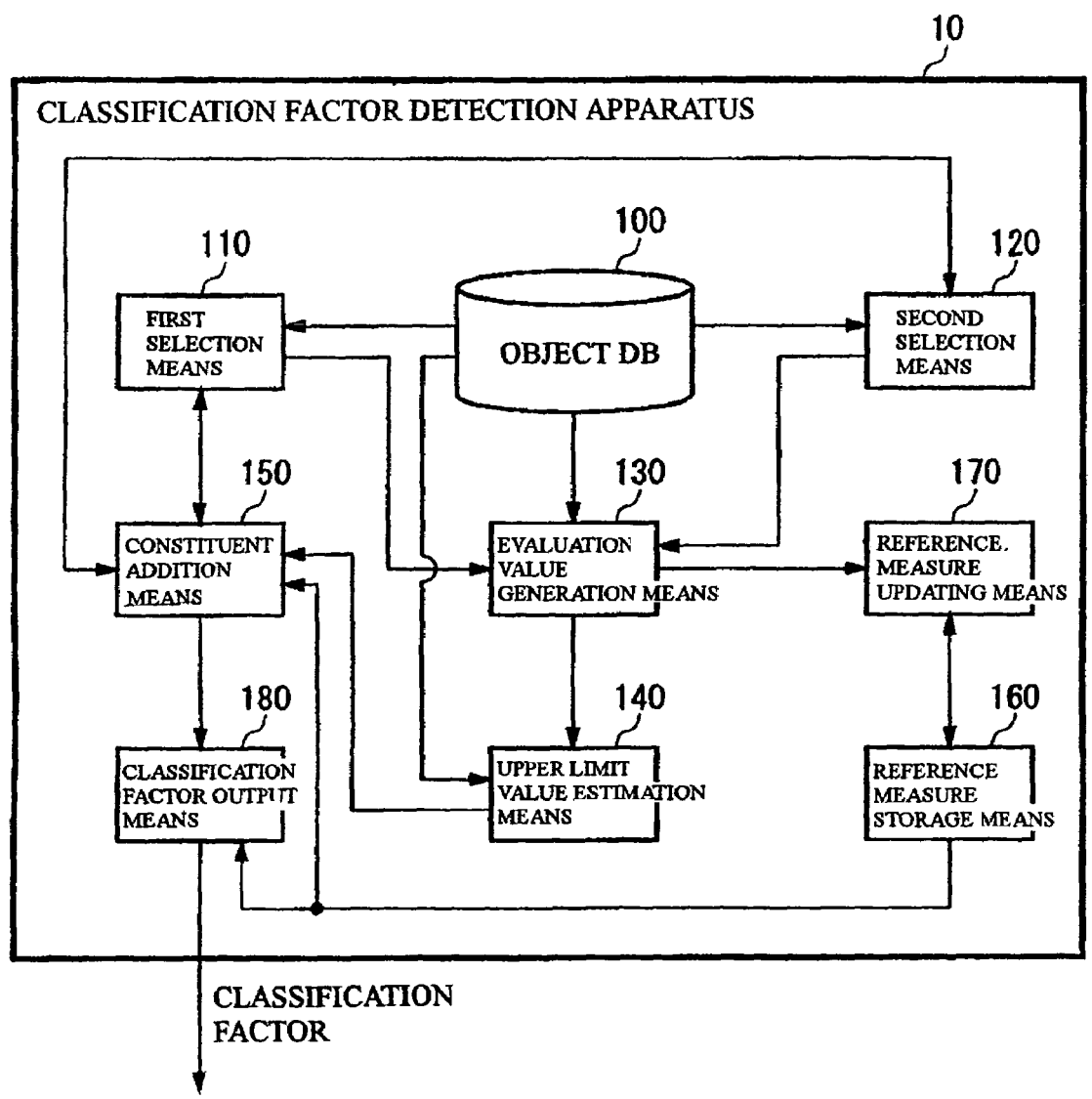

[Figure 2]
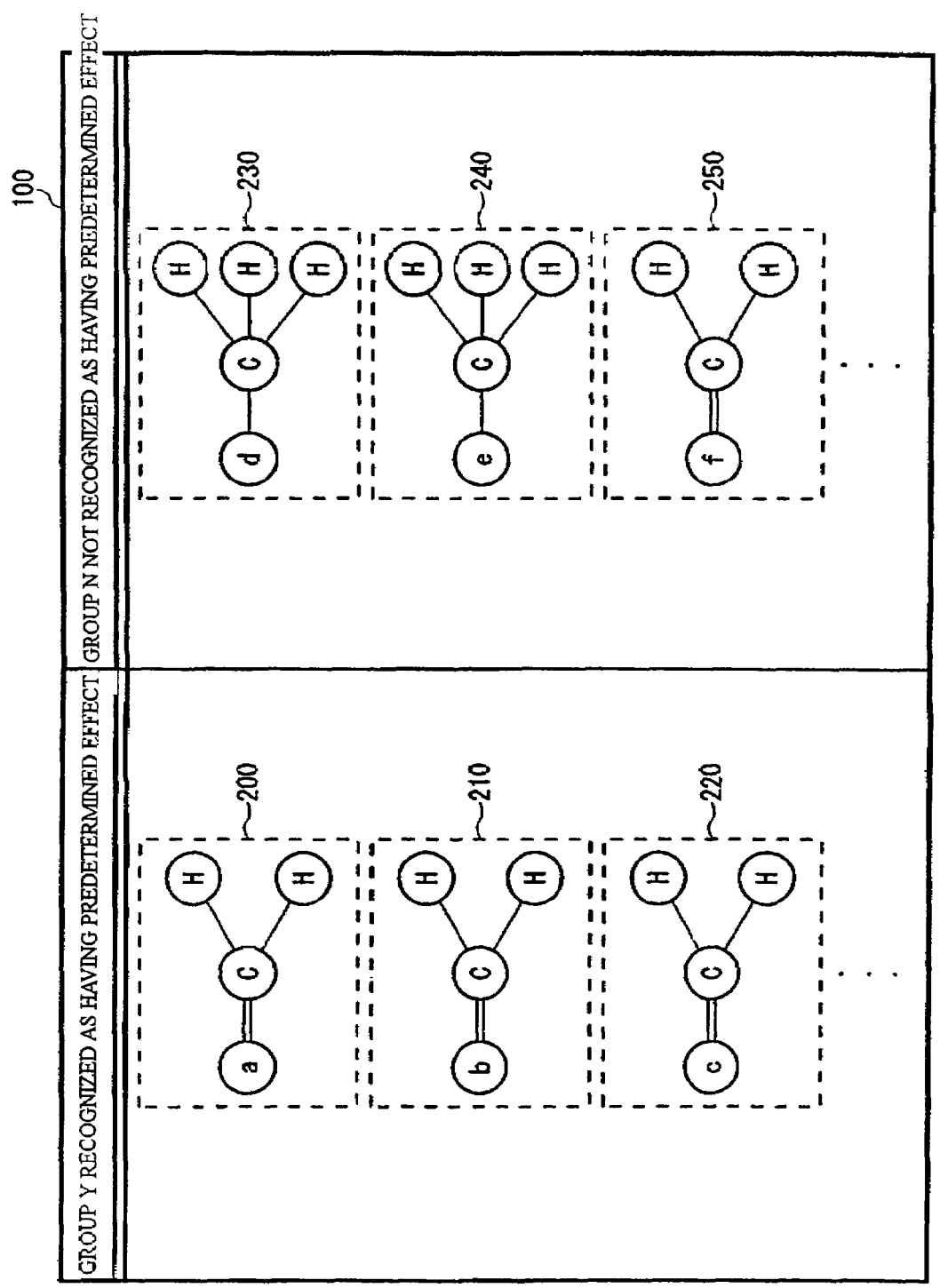

[Figure 3]
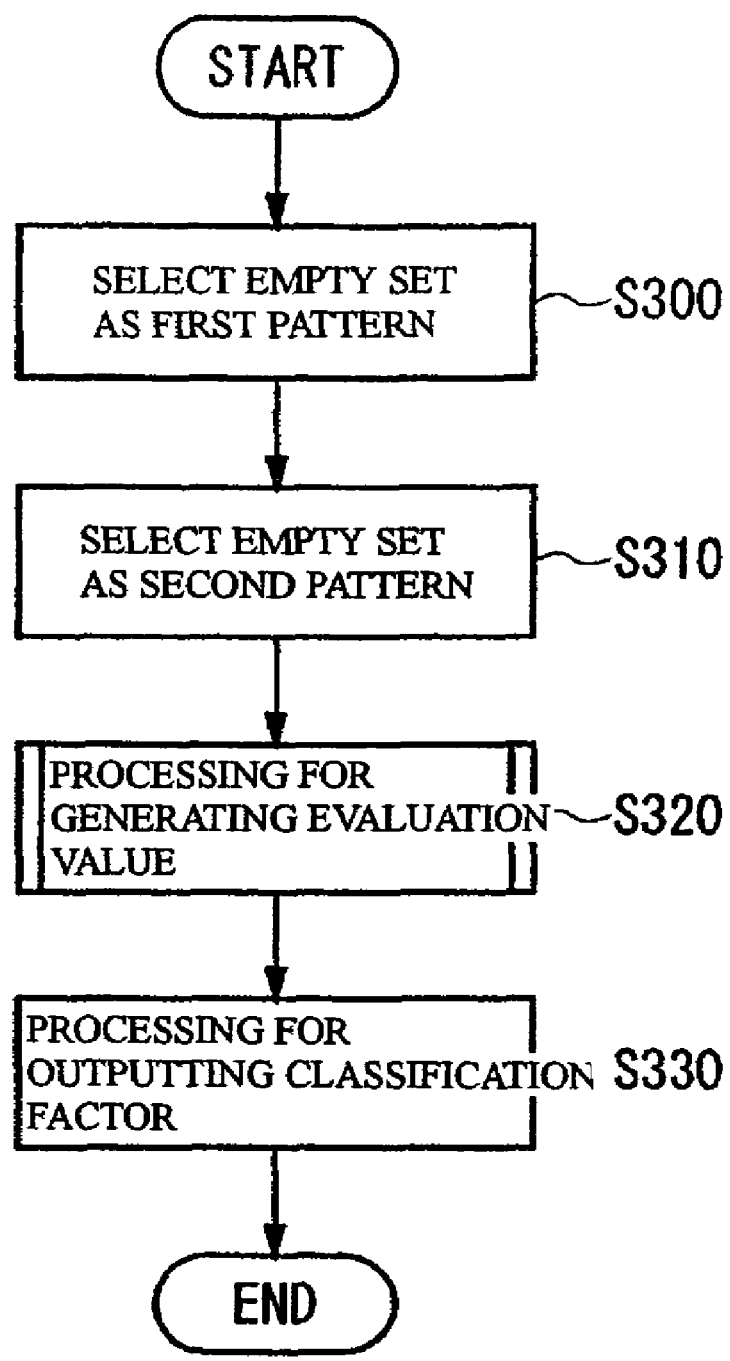

[Figure 4]
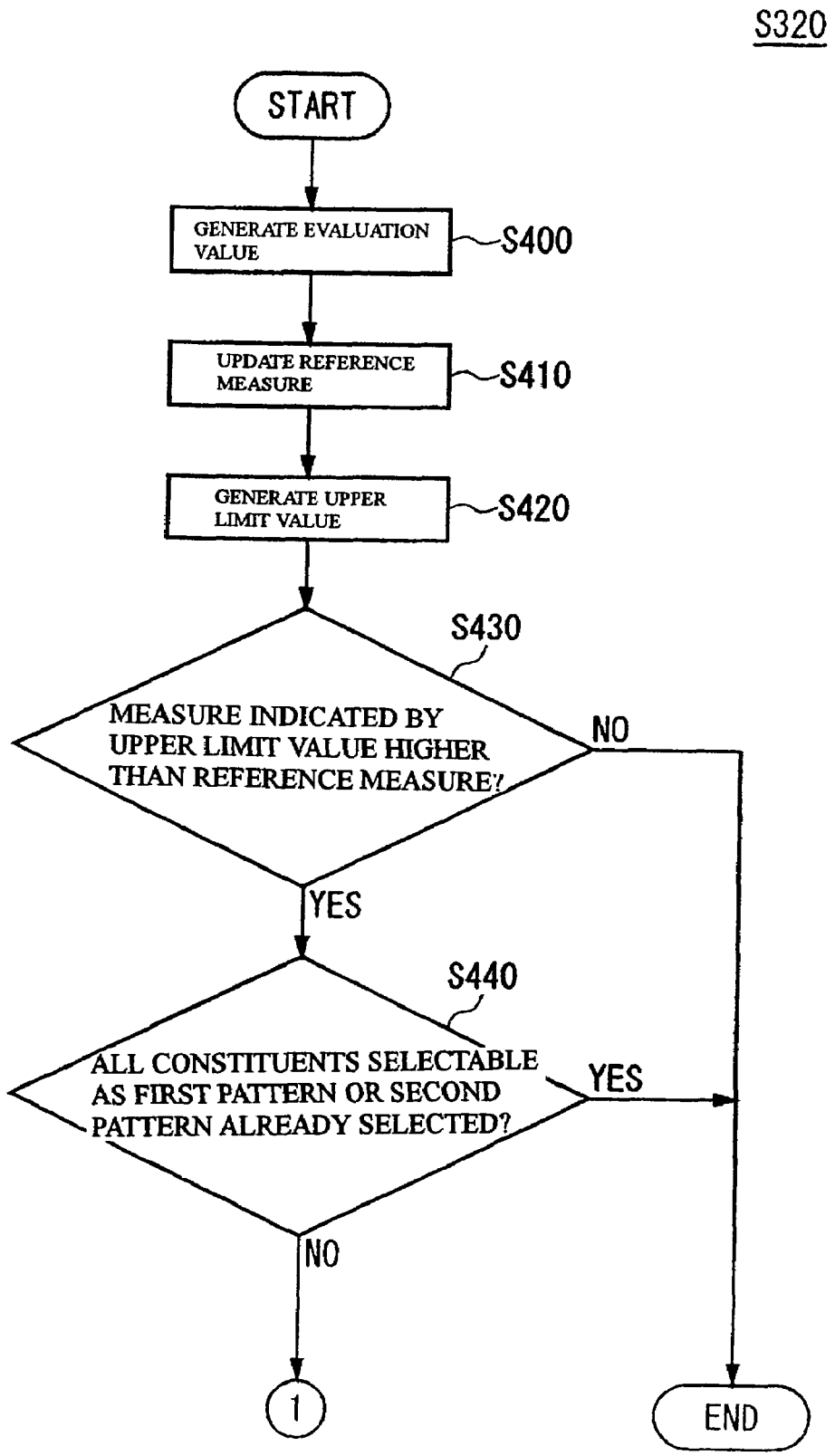

[Figure 5]
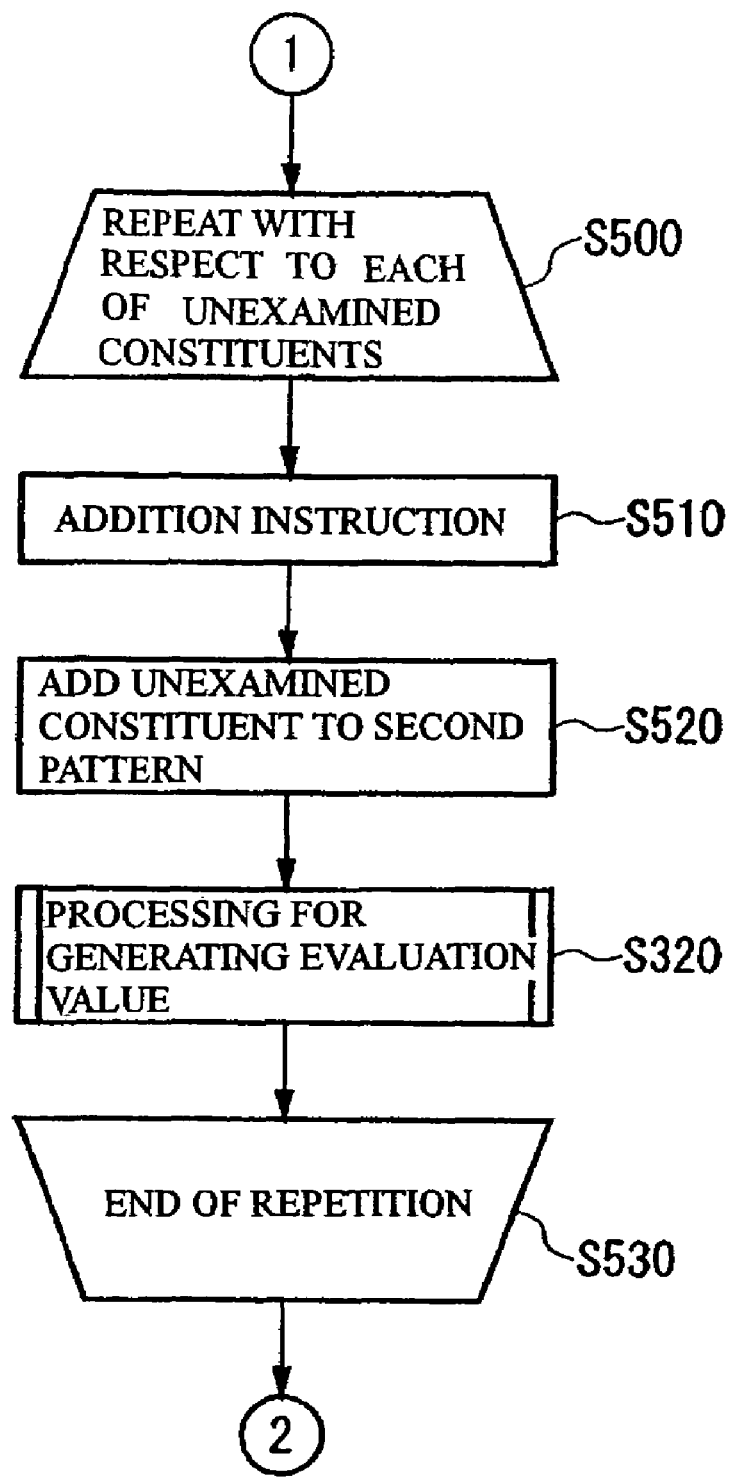

[Figure 6]
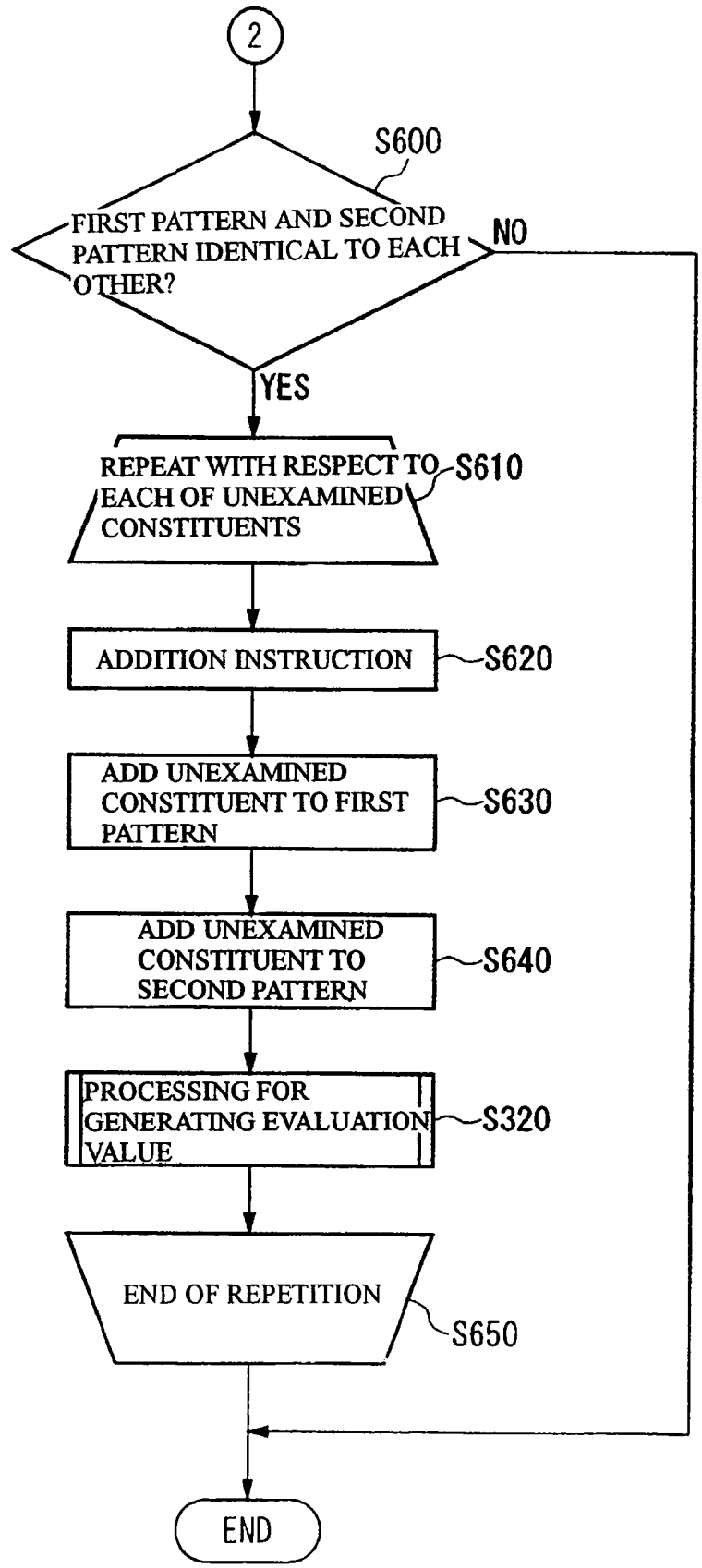

[Figure 7]

| CLASS Y | CLASS N | SUM OF ROWS | SUM OF COLUMNS |
|---|---|---|---|
| $P_1\overline{P_2}$ | $O_{I c} = a - c$ | $O_{I\bar{c}} = b - d$ | $O_I$ |
| $\overline{P_1\overline{P_2}}$ | $O_{\bar{I}c}$ | $O_{\bar{I}\bar{c}}$ | $O_{\bar{I}}$ |
| | $O_c = y$ | $O_{\bar{c}} = n$ | $y + n$ |

[Figure 8]
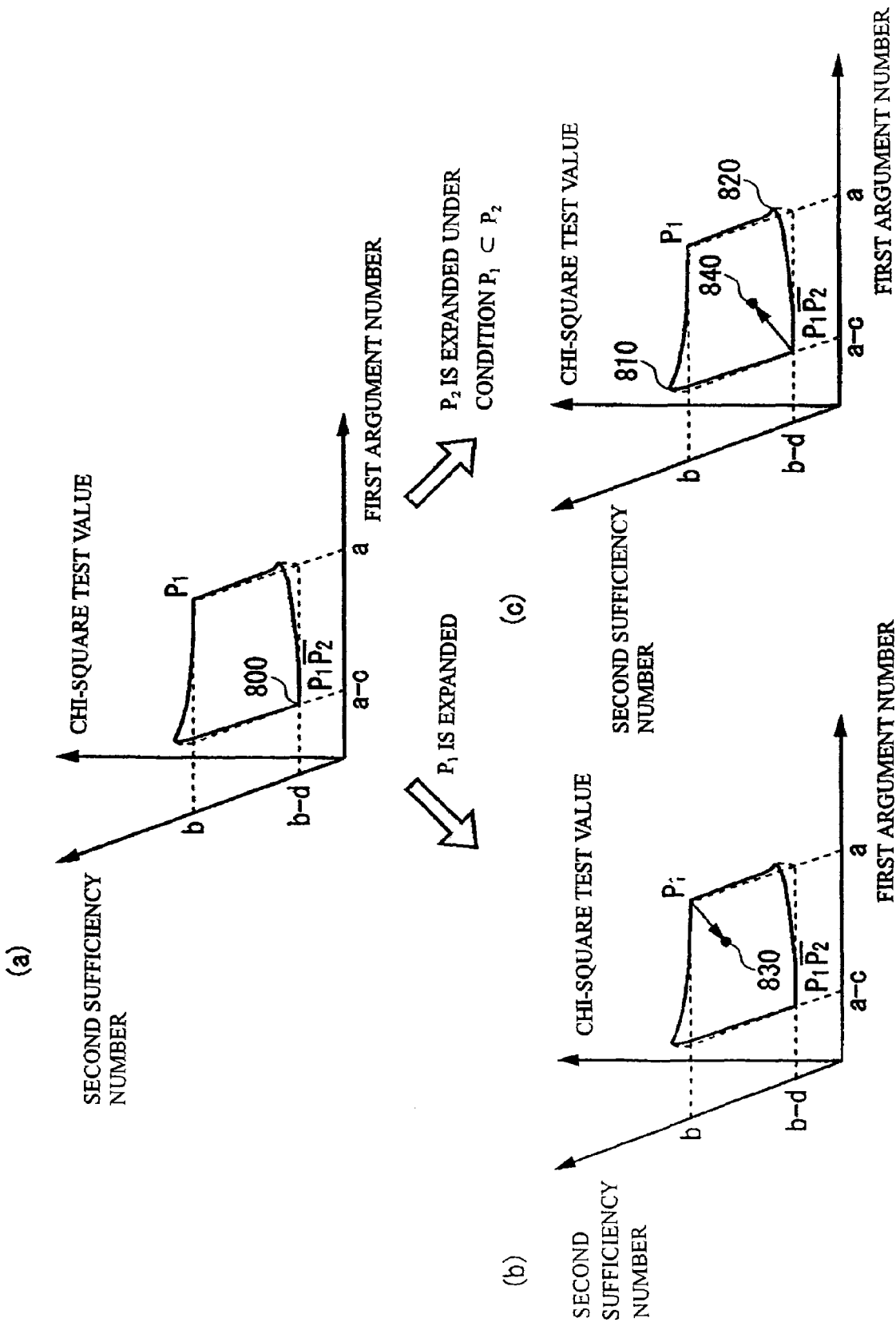

[Figure 9]
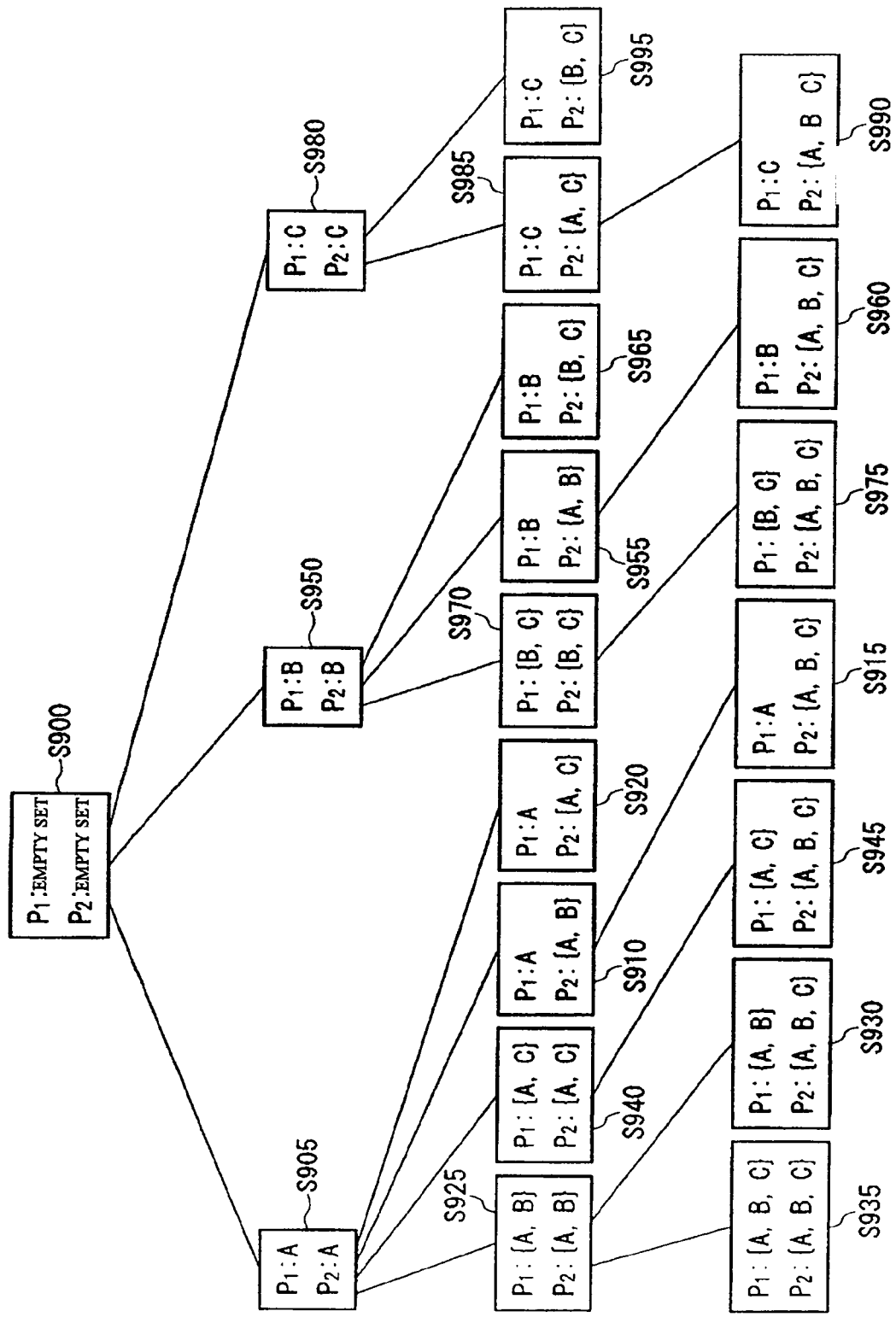

[Figure 10]
(a)
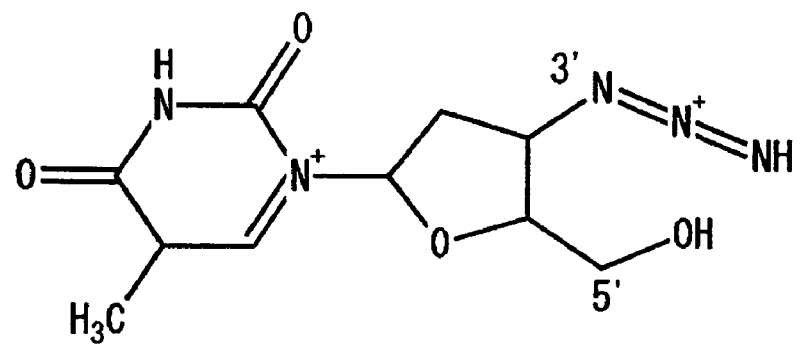
(b)
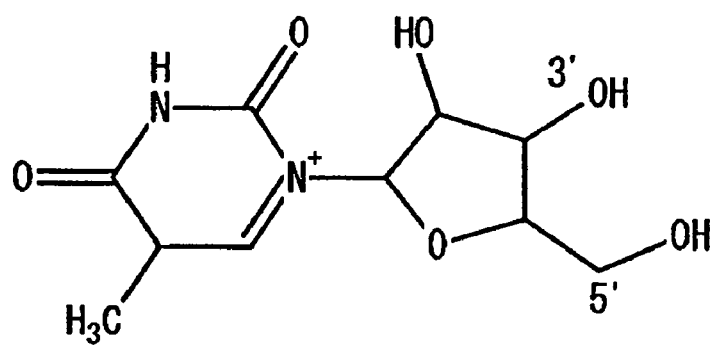
(c)
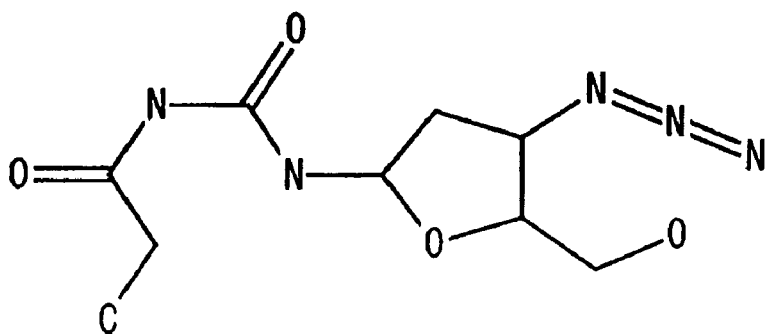

[Figure 11]
(a)
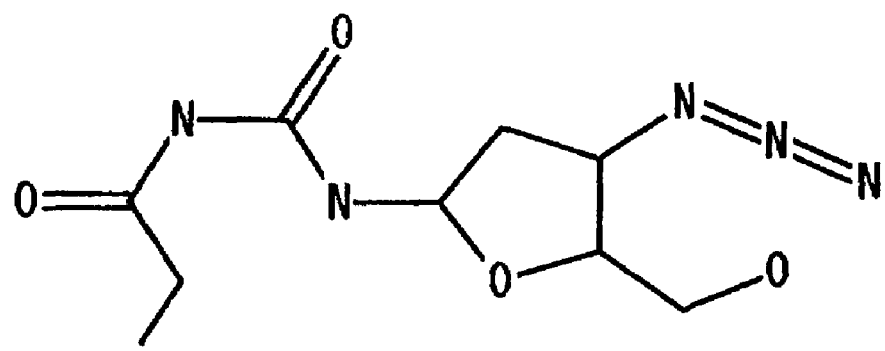
(b)
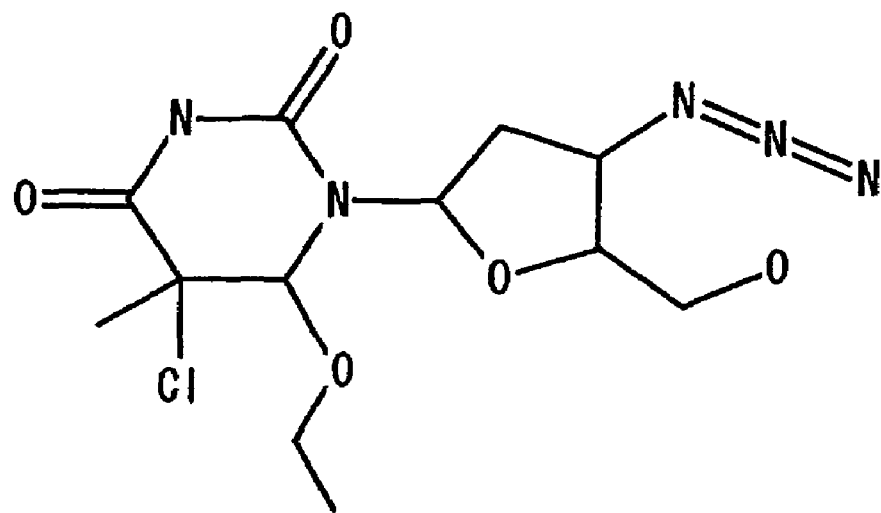

[Figure 12]
(a)
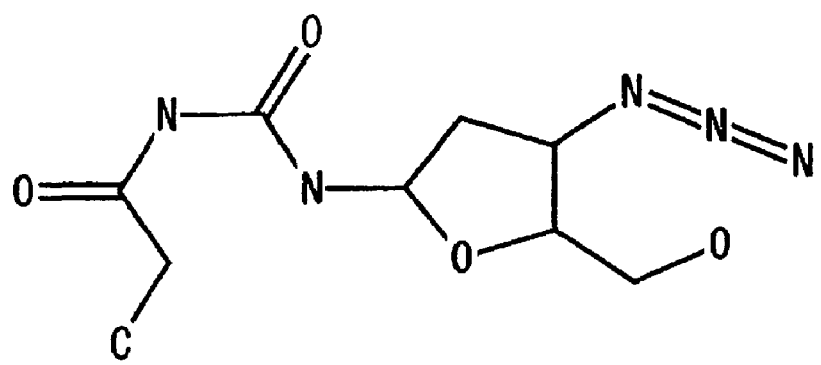
(b)
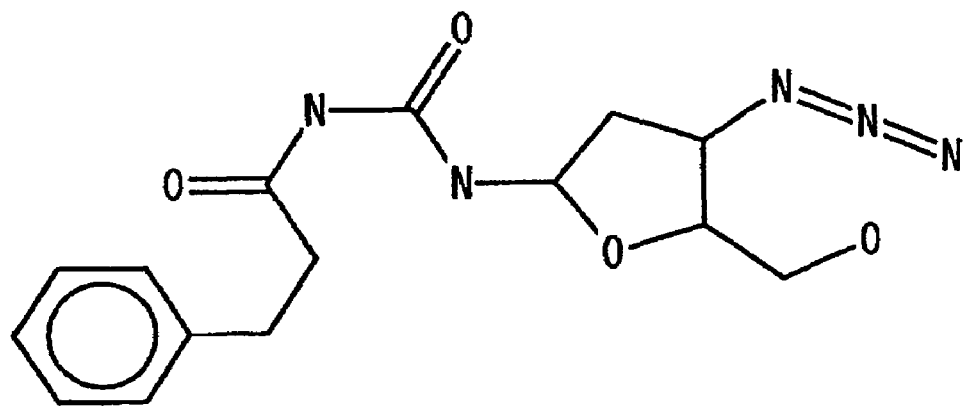

[Figure 13]

| DOMESTIC ECONOMIC NEWS GROUP Y | INTERNATIONAL ECONOMIC NEWS GROUP N |
|---|---|
| PRICE OF AA FELL SHARPLY ON TOKYO MARKET... | INTERNATIONAL COORDINATION IS REQUIRED FOR STABILIZATION OF PRICE OF BB |
| PRICE OF CC ROSE UNDER SAFEGUARD... | DISCUSSIONS WERE MADE ABOUT ANTI-TERRORISM MEASURES... |
| WITH INCREASE IN PRICE OF EE, PRICES OF COMMODITIES... | CONFERENCE REGARDING PRICE OF CUSTOM DUTY ON DD WAS... |
| ... | ... |

[Figure 14]
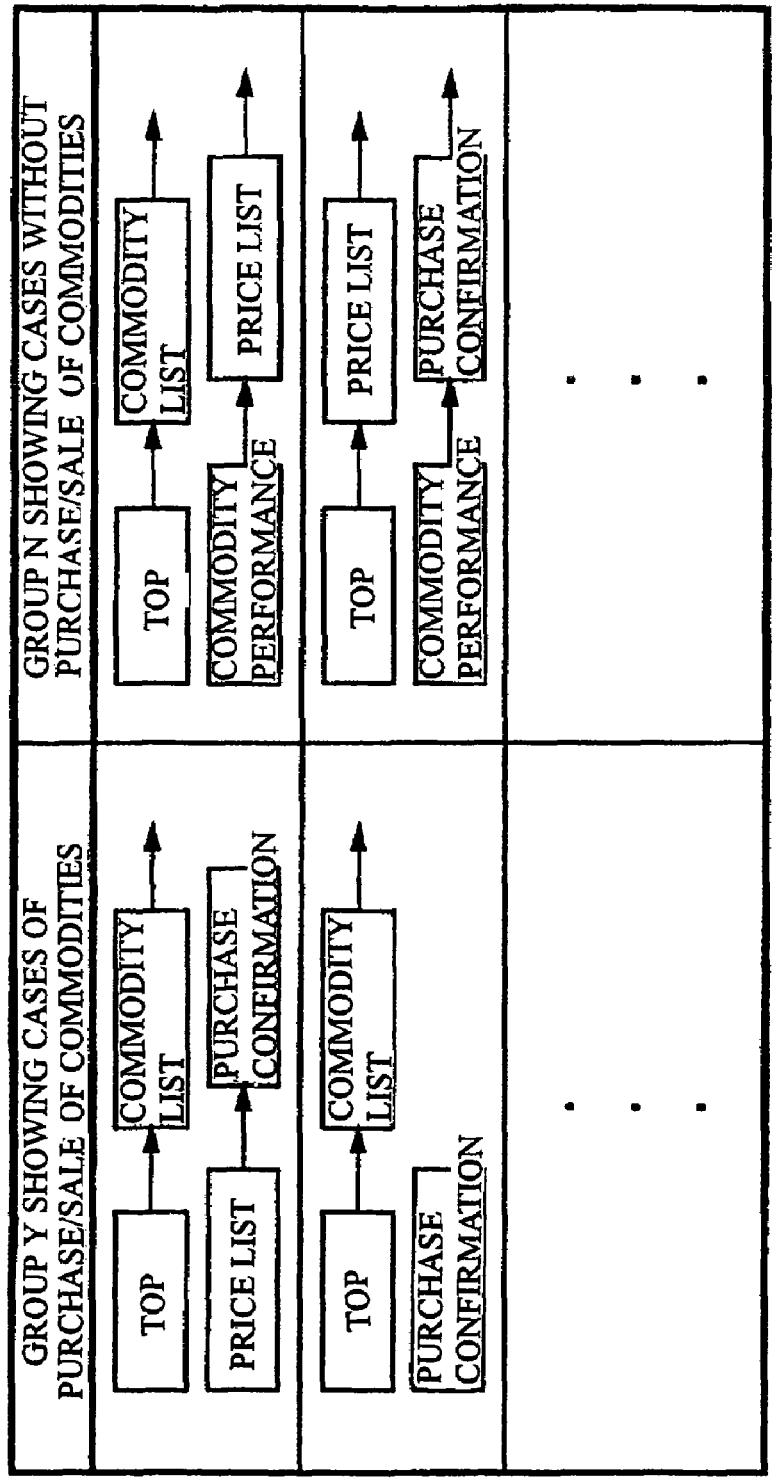

[Figure 15]
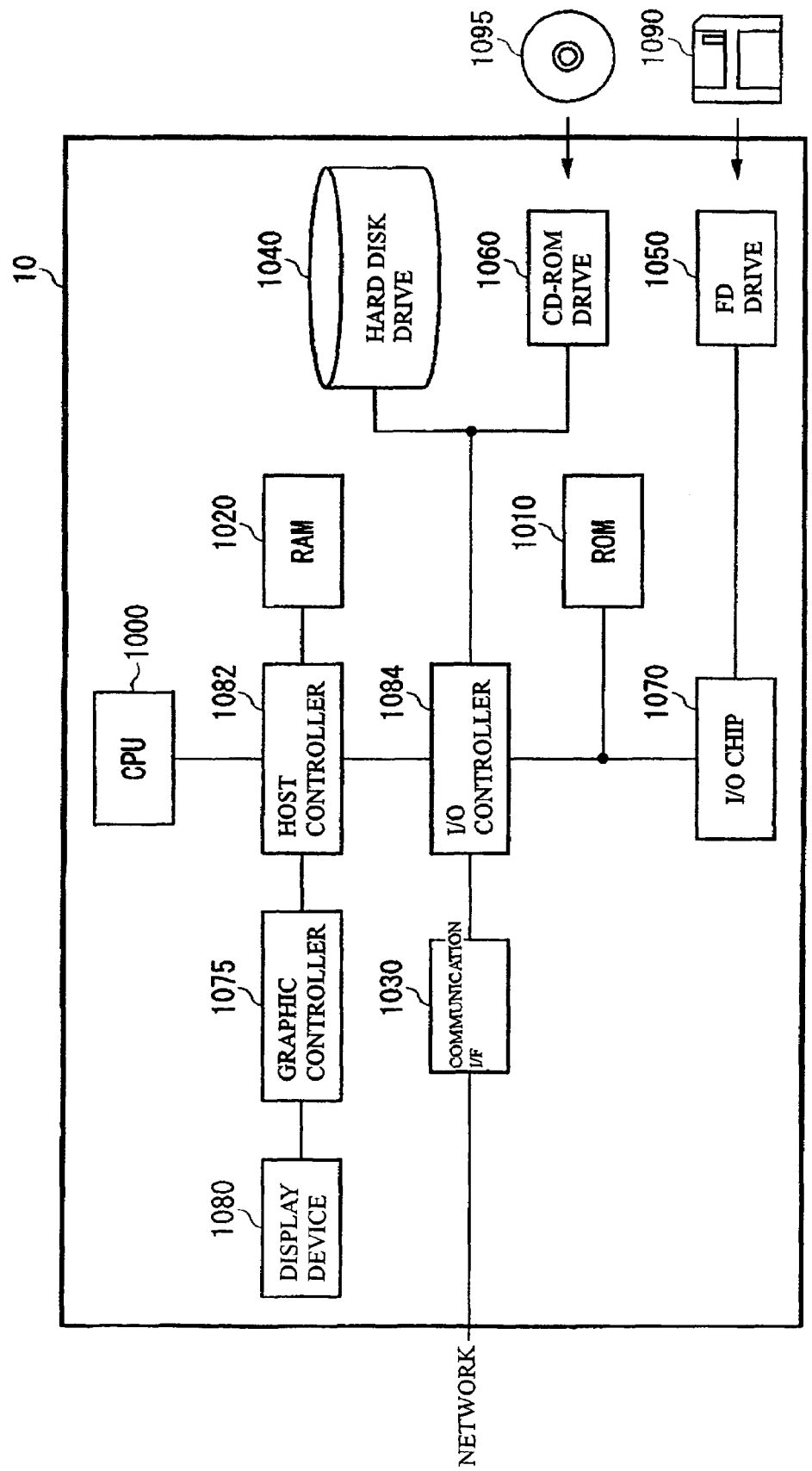

CLASSIFICATION FACTOR DETECTION

FIELD OF THE INVENTION

The present invention relates to classification factor detection. More particularly, the present invention relates to a classification factor detection apparatus, method, program and recording medium, which detect a structure which is a factor for classification

BACKGROUND

In recent years, with the introduction of IT (information technology) in various fields, the electronification of data on materials in the natural world, social phenomena, human behaviors, etc., has progressed. With this background, data mining techniques of detecting frequently appearing patterns from a large amount of accumulated data and effectively utilizing the detected patterns for business and scientific purposes are attracting attention.

The following documents are considered:

Non-patent Document 1
Alberts, B., Bray, D., Johnson, A., Lewis, J., Raff, M., Roberts, K., & Walter, P., Translation Supervisors: Nakamura Keiko, Fujiyama Asao and Matubara Kenichi. Essential Cell Biology. Nankodo.

Non-patent Document 2
Asai Tatuya, Abe Kenji, Kawazoe Shinji, Hiroki Arimura, and Setuo Arikawa. Efficient search for partial structure pattern for semistructured data mining. Technical Report from Data Engineering Technical Group in the Institute of Electronics, Information and Communication Engineers, Vol. 101, No. 342, 1-8.

Non-patent Document 3
Cook, D. J., & Holder, L. B. (1994). Substructure Discovery Using Minimum Description Length and Background Knowledge. Journal of Artificial Intelligence Research, Vol. 1, (pp. 231-255).

Non-patent Document 4
Dehaspe, L., Toivonen, H., & King, R. D. (1998). Finding frequent substructures in chemical compounds. Proc. of the 4th KDD, (pp. 30-36).

Non-patent Document 5
De Raedt, L., & Kramer, S. (2001). The Levelwise version Space Algorithm and its Application to Molecular Fragment Finding. Proc. of the 17th IJCAI, (pp. 853-859).

Non-patent Document 6
AIDS Antiviral Screen, http://dtp.nci.nih.gov/docs/aids/aids_data.html Non-patent Document 7
Inokuchi, I., Washio, T., & Motoda, H. (2000). An Apriori-based Algorithm for Mining Frequent Substructures from Graph Data. Proc. of the 4th PKDD, (pp 12-23).

Non-patent Document 8
Inokuchi, A., Washio, T., Nishimura, Y., & Motoda, H. A Fast Algorithm for Mining Frequent Connected Subgraphs. IBM Research Report, RT0448 (February, 2002).

Non-patent Document 9
Inokuchi, Akihiro, Washio Takashi, Nishimura Yoshio, and Motoda Hiroshi. Method of extracting connected frequent graphs from graph-structured data. The 16th Annual Conference of the Japanese Society for Artificial Intelligence, 1 A3-03, (2002).

Non-patent Document 10
Inokuchi, Akihiro, Washio Takashi, Nishimura Yoshio, and Motoda Hiroshi. Data mining on HIV data. The 58th Special Interest Group on Knowledge Base System, (2002).

Non-patent Document 11
Kramer, S., De Raedt, L., & Helma, C. (2001). Molecular Feature Mining in HIV Data. Proc. of the 17th International Conference on Knowledge Discovery and Data Mining, (pp. 136-143).

Non-patent Document 12
Kuramochi, M., & Karypis, G. (2001) Frequent Subgraph Discovery. Procs. of the 1st ICDM.

Non-patent Document 13
Kuramochi, M., & Karypis, G. Discovering Frequent Geometric Subgraphs. Technical Report 02-024, 2002.

Non-patent Document 14
Matsuda, T., Horiuchi, T., Motoda, H., & Washio, T. (2000). Extension of Graph-Based Induction for General Graph Structured Data. Proc. of the 4th PAKDD, (pp. 420-431).

Non-patent Document 15
Matsumoto Takatoshi and Tanabe Kazutoshi. Prediction of Carcinogenicity of Chlorine-containing Organic Compound by Neural Network. JCPE Journal, Vol. 11, No. 1, 29-34 (1999)

Non-patent Document 16
Matsuzawa, H., & Fukuda, T., Mining Structured Association Patterns from Databases. Proc. of the 4th Pacific-Asia Conference on Knowledge Discovery and Data Mining.

Non-patent Document 17
T. Miyahara, T. Uchida, T., Shoudai, T., Kuboyama, K. Takahashi and H. Ueda: Discovery of Frequent Tree Structured Patterns in Semistructured Data. Proc. of the 5th Pacific-Asia Conference on Knowledge Discovery and Data Mining, pp. 1-10, 2001.

Non-patent Document 18
Morimoto Yasuhiko. Algorithm for counting frequent sets from spatial database. The 2nd Data Mining Workshop, pp. 1-10.

Non-patent Document 19
Morishita, S. and Sese, J. (2000), Traversing Lattice Itemset with Statistical Metric Pruning. Proc. of POS 2000.

Non-patent Document 20
Motoda, H., & Yoshida, K. (1997). Machine Learning Techniques to Make Computers Easier to Use. Proc. of the 15th IJCAI, Vol. 2, (pp. 1622-1631).

Non-patent Document 21
Wang, X., Wang, J., Shasha, D., Shapiro, B., Dikshitulu, S., Rigoutsos, I., & Zhang, K. Automated Discovery of Active Motifs in Three Dimensional Molecules. Proc. of the 3rd International Conference on KDD. pp. 89-95. (1997)

Non-patent Document 22
Wang, X., Wang, J., Shasha, D., Shapiro, B., Rigoutsos, I., & Zhang, K. Finding Patterns in Three-dimensional Graphs: Algorithms and Applications to Scientific Data Mining. IEEE Transactions on Knowledge and Data Engineering, Vol. 14 No. 4 pp. 731-749. (2002)

Non-patent Document 23
Yoshida, K., & Motoda, H. (1995). CLIP: Concept Learning from Inference Patterns. AI, Vol. 75, No. 1 pp. 63-92

Non-patent Document 24
Zaki, M. Efficiently Mining Frequent Trees in a Forest. Proc. of the 8th International Conference on KDD.

A method of detecting a frequently appearing pattern from relations stored in a relational table or a typical log such as POS transactions has been proposed. (See non-patent document 18).

A method of detecting a frequently appearing pattern from graph- or tree-structured data as well as from a typical log has also been proposed. (See non-patent documents 4, 5, 7, 8, 9, and 12 with respect to techniques for data mining on graph-structured data, and see non-patent documents 2, 16, and 24 with respect to techniques for data mining on tree-structured data).

A data mining technique of detecting a frequently appearing pattern from tree-structured or graph-structured data can find applications in various fields, e.g., applications to pattern detection from the molecular structure of chemical materials, results of syntax analysis on a natural language, the modification structure of words in a natural language.

For additional background, see other related non-patent documents 1, 3, 6, 10, 11, 13, 14, 15, 17, 18, 19, 20, 21, 22, and 23.

The present invention solves problems related to the above. The problems to be solved include the following considerations. The conventional techniques reside in detecting a single frequently appearing pattern in a group of data satisfying a predetermined condition. For example, a finding that data including a frequently appearing pattern can easily satisfy a predetermined condition has been obtained thereby. In some cases, however, a more suitable finding is required depending on the kind of data to be processed, etc.

For example, in the field of chemistry, novel chemical materials are synthesized one after another to be used as chemicals for people's living and health. On the other hand, side effects of such chemical materials are a consideration. Therefore, there is a need to evaluate the hazardousness of chemical materials, e.g., the degradability and accumulability under natural environmental conditions including the air, water and soil, and the accumulability, condensability, etc., in the interior of living things. However, many years and a high cost are required for experimental evaluation of the hazardousness of chemical materials.

If the effectiveness and hazardousness of chemical materials can be nonexperimentally evaluated, the time and cost can be largely reduced (See non-patent document 15). The conventional data mining techniques enable each of patterns considered to be a factor of the effectiveness of a chemical material and patterns considered to be a factor of the hazardousness of the chemical material to be separately detected. However, it is difficult to suitably perform detection under a predetermined combination of conditions, e.g., detection of a chemical material having a certain degree of effectiveness while having a low degree of hazardousness by using any of the conventional techniques.

SUMMARY OF THE INVENTION

It is, therefore, an aspect of the present invention to provide a classification factor detection apparatus capable of solving the above-described problem, and to a relating classification factor detection method, program and recording medium.

In an example embodiment of the present invention, there is provided a classification factor detection apparatus which detects, with respect to the results of classification into two groups of a plurality of objects each constituted by a plurality of constituents through analysis as to whether or not each object has a predetermined characteristic, a set of some of the constituents as a factor of the classification, the apparatus having first selection means of selecting a first pattern which is a set of at least one of the plurality of constituents of one of the plurality of objects, second selection means of selecting, from the plurality of constituents in one of the plurality of objects, a second pattern formed of the first pattern and at least one of the constituents added to the first pattern, evaluation value generation means of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, and classification factor output means of outputting the constituents in each of the first pattern and the second pattern as a factor of classification when the measure indicated by the evaluation value exceeds a reference measure determined in advance, a classification factor detection method of making a computer function as the apparatus, a program for making a computer function as the apparatus, and a recording medium on which the program is recorded.

According to the present invention, a suitable set of conditions can be detected as a condition for classification of data.

BRIEF DESCRIPTION OF THE DRAWINGS

These and other objects, features, and advantages of the present invention will become apparent upon further consideration of the following detailed description of the invention when read in conjunction with the drawing figures, in which:

FIG. 1 is a block diagram of a classification factor detection apparatus 10;

FIG. 2 shows an example of the contents of an object database 100;

FIG. 3 shows an operation flow of the classification factor detection apparatus 10;

FIG. 4 shows details of S320 in the operation flow shown in FIG. 3;

FIG. 5 shows an operation flow following that in FIG. 4;

FIG. 6 shows an operation flow following that in FIG. 5;

FIG. 7 shows a table in which the data shown in FIG. 2 is classified;

FIG. 8(a) shows an evaluation value generated by evaluation value generation means 130.

FIG. 8(b) is a diagram for explaining the upper limit value when one of the constituents is added to the first pattern.

FIG. 8(c) is a diagram for explaining the upper limit value when one of the constituents is added to the second pattern;

FIG. 9 shows an example of a search tree showing the order of search for classification conditions satisfying a reference measure;

FIG. 10(a) shows an example of a chemical material recognized as having pharmacological activity through predetermined analysis.

FIG. 10(b) shows an example of a chemical material relating to that shown in FIG. 10(a).

FIG. 10(c) shows an example of a structure detected as a pattern having pharmacological activity by a method different from that in the embodiment;

FIG. 11(a) shows an example of the first pattern output as a factor of classification by the classification factor detection apparatus 10.

FIG. 11(b) shows an example of the second pattern output as a factor of classification by the classification factor detection apparatus 10;

FIG. 12(a) shows another example of the first pattern output as a factor of classification by the classification factor detection apparatus 10.

FIG. 12(b) shows another example of the second pattern output as a factor of classification by the classification factor detection apparatus 10;

FIG. 13 shows an example of outputting of a factor for classification of news items;

FIG. 14 shows an example of outputting of a factor for classification of Web page browse records; and FIG. 15 shows an example of a hardware configuration of the classification factor detection apparatus 10.

DESCRIPTION OF SYMBOLS

10 Classification factor detection apparatus
100 Object database
110 First selection means
120 Second selection means
130 Evaluation value generation means
140 Upper limit value estimation means
150 Constituent addition means
160 Reference measure storage means
170 Reference measure updating means
180 Classification factor output means
200 Chemical material
210 Chemical material
220 Chemical material
230 Chemical material
240 Chemical material
250 Chemical material
800 Evaluation value
810 Upper limit candidate value
820 Upper limit candidate value
830 Evaluation value
840 Evaluation value

DETAILED DESCRIPTION OF THE INVENTION

The present invention provides classification factor detection apparatus, methods, systems and programs to detect, with respect to the results of classification into two groups of a plurality of objects each constituted by a plurality of constituents through analysis as to whether or not each object has a predetermined characteristic, a set of some of the constituents as a factor of the classification.

An example apparatus having first selection means of selecting a first pattern which is a set of at least one of the plurality of constituents of one of the plurality of objects, second selection means of selecting, from the plurality of constituents in one of the plurality of objects, a second pattern formed of the first pattern and at least one of the constituents added to the first pattern, evaluation value generation means of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, and classification factor output means of outputting the constituents in each of the first pattern and the second pattern as a factor of classification when the measure indicated by the evaluation value exceeds a reference measure determined in advance, a classification factor detection method of making a computer function as the apparatus, a program for making a computer function as the apparatus, and a recording medium on which the program is recorded.

The present invention will be described with respect to an advantageous embodiment thereof. The embodiment described below, however, is not limiting of the invention set forth in the appended claims, and all combinations of features described in the description of the embodiment are not necessarily indispensable to the solution according to the present invention.

FIG. 1 is a functional block diagram of a classification factor detection apparatus 10. The classification factor detection apparatus 10 is an apparatus designed to detect, with respect to the results of classification into two groups of a plurality of objects each constituted by a plurality of constituents through analysis as to whether or not each object has a predetermined characteristic, a set of some of the constituents as a factor of the classification. More specifically, the classification factor detection apparatus 10 generates a plurality of classification conditions on the basis of constituents of objects and searches the plurality of classification conditions for those having an evaluation value (e.g., a chi-square test value) higher than a predetermined value of the measure that the objects can be classified. The classification factor detection apparatus 10 can save the search time by estimating an upper limit value of the evaluation value thereafter generated in the process of changing the classification conditions and generating the evaluation value and by stopping the search if the upper limit value is equal to or smaller than the predetermined value.

The classification factor detection apparatus 10 has an object database 100, a first selection means 110, a second selection means 120, an evaluation value generation means 130, an upper limit value estimation means 140, a constituent addition means 150, a reference measure storage means 160, a reference measure updating means 170, and a classification factor output means 180.

In the object database 100, a plurality of objects classified into two groups are stored. The first selection means 110 selects a first pattern, which is a set of at least one of the plurality of constituents of one of the plurality of objects, from the object database 100 on the basis of an instruction from the constituent addition means 150, and sends the selected first pattern to the evaluation value generation means 130. If all the selectable constituents in the object database 100 have already been selected, the first selection means 110 sends information describing this state to the constituent addition means 150.

The second selection means 120 selects a second pattern formed of the first pattern and at least one of the constituents added to the first pattern from the object database 100 on the basis of an instruction from the constituent addition means 150, and sends the selected second pattern to the evaluation value generation means 130. If all the selectable constituents in the object database 100 have already been selected, the second selection means 120 sends information describing this state to the constituent addition means 150.

The evaluation value generation means 130 generates, on the basis of the contents of the object database 100, a first argument number which is the number of objects satisfying a classification condition including the first pattern and not including the second pattern in the plurality of objects classified into the first group, and a second argument number which the number of objects satisfying this classification condition in the plurality of objects classified into the second group. The evaluation value generation means 130 generates, on the basis of the first argument number and the second argument number, an evaluation value, e.g., a chi-square test value of the measure of classification of the plurality of objects under the classification condition, and sends the evaluation value to the reference measure updating means 170 by relating the evaluation value to the first pattern and the second pattern at the time of generation of the evaluation value. The evaluation value generation means 130 also sends the classification condition to the upper limit value estimation means 140.

The upper limit value estimation means 140 generates, on the basis of the contents of the object database 100, an upper limit value of the evaluation value in a possible region for the first argument number and the second argument number when one of the constituents is added to the first pattern and the second pattern, and sends the upper limit value to the constituent addition means 150.

The constituent addition means 150 sends instructions to the first selection means 110 and the second selection means 120 to successively perform first addition processing for adding one of the constituents to the second pattern and second addition processing for adding the same constituent to the first pattern and the second pattern when the measure indicated by the upper limit value received from the upper limit value estimation means 140 is higher than a reference measure received from the reference measure storage means 160.

More specifically, the constituent addition means 150 stores details of addition processing to be successively performed in a data structure such as a stack in a memory when the measure indicated by the upper limit value received from the upper limit value estimation means 140 is higher than the reference measure. Each time the constituent addition means 150 receives the upper limit value from the upper limit value estimation means 140, it performs each addition processing according to the storage contents in the memory regardless of whether or not the measure indicated by the upper limit value is higher than the reference measure.

When the constituent addition means 150 receives from each of the first selection means 110 and the second selection means 120 the notice that all the selectable constituents have been selected, it terminates the evaluation value generation processing and sends a termination instruction to the classification factor output means 180 to output a classification factor.

The reference measure storage means 160 stores a predetermined reference measure. The reference measure updating means 170 obtains an evaluation value from the evaluation value generation means 130 with reference to the first pattern and the second pattern at the time of generation of the evaluation value. If the measure indicated by the evaluation value exceeds the reference measure stored in the reference measure storage means 160, the reference measure updating means 170 stores the measure indicated by the evaluation value as the reference measure in the reference measure storage means 160 by relating it to the first pattern and the second pattern at the time of generation of the evaluation value.

In this manner, the reference measure storage means 160 can store the maximum of evaluation values already generated. The reference measure storage means 160 may further store the reference measure before replacement. In such a case, the reference measure storage means 160 can store not only the maximum of evaluation values but also each of a plurality of evaluation values indicating a measure exceeding the reference measure by relating the evaluation value to the first pattern and the second pattern at the time of generation of the evaluation value.

When the classification factor output means 180 receives a termination instruction from the constituent addition means 150, it obtains the maximum of evaluation values and some other values by relating it to the first pattern and the second pattern at the time of generation of the corresponding evaluation value. The classification factor output means 180 outputs the constituents in each of the first pattern and the second pattern as a factor of classification.

Thus, the classification factor detection apparatus 10 can detect, as a factor of classification, not only a condition as to whether or not a predetermined pattern is included but also a predetermined combination of conditions, e.g., a classification condition including a first pattern but not including a second pattern. In this manner, a suitable classification factor, e.g., a chemical structure having a predetermined effect as a drug and having no considerable side effect can be detected in various fields of application.

FIG. 2 shows an example of the contents of the object database 100. In the object database 100, a plurality of objects classified into two groups are stored. In the example shown in FIG. 2, the objects are chemical materials in which a plurality of elements, i.e., a plurality of constituents, bond chemically together. The plurality of objects are classified into a group Y recognized as having a predetermined effect and a group N not recognized as having the predetermined effect on the basis of determination by experiment as to whether or not each chemical material has the predetermined effect as a drug.

Analysis in accordance with the present invention as to whether or not an object has a predetermined characteristic is, for example, an experiment as to whether or not an object has a predetermined effect as a drug as described with respect to this example. Alternatively, analysis as to whether or not an object has a predetermined characteristic may be analysis as to whether or not a content of a sentence belongs to a predetermined genre or analysis as to whether or not a reader has performed a predetermined action as a result of reading a Web page. That is, analysis as to whether or not an object has a predetermined characteristic may be a determination as to whether or not the object has a certain characteristic made on the basis of an experiment, a measurement or observation performed in advance no matter what the kind of the object.

In the object database 100, a chemical material 200 including a predetermined molecular structure "a", carbon with a double bond to the molecular structure "a" and two hydrogens each bonded to carbon, a chemical compound 210 corresponding generally in structure to the chemical material 200 and having a molecular structure "b" instead of the molecular structure "a" and a chemical compound 220 corresponding generally in structure to the chemical material 200 and having a molecular structure "c" instead of the molecular structure "a" are stored as group Y.

Also, in the object database 100, a chemical material 230 including a predetermined molecular structure "d", carbon bonded to the molecular structure "d" and three hydrogens each bonded to carbon, a chemical compound 240 corresponding generally in structure to the chemical material 230 and having a molecular structure "e" instead of the molecular structure "d" and a chemical compound 250 having a predetermined molecular structure "f", carbon with a double bond to the molecular structure "f" and two hydrogens each bonded to carbon are stored as group N.

Description will be made of an example of a case where a combination of a double bond to carbon, carbon and a pair of hydrogens each bonded to carbon contributes greatly to pharmacological activity through which the material exhibits a predetermined effect as a drug. In other methods of detecting a pattern having a predetermined effect, there is a possibility of a combination of carbon and a pair of hydrogens each bonded to the carbon being detected as a candidate of a pattern having the predetermined effect as a drug. However, such a detected pattern candidate is also included in each of the chemical materials 230, 240 and 250 classified into the group N. Therefore, such a combination is not liable to be detected as a factor of classification of the plurality of objects into the group Y and the group N.

Thus, in other methods, there is a possibility of failure to suitably detect an essential factor of classification. In contrast, the classification factor detection apparatus 10 detects as a first pattern a combination of carbon and a pair of hydrogens each bonded to the carbon and as a second pattern a combination of carbon and three hydrogens each bonded to the carbon, thereby enabling a classification condition based on the first pattern and the second pattern to be detected as a factor of classification into the group Y and the group N.

More specifically, the evaluation value generation means 130 computes 3 as a first argument number which is the number of objects satisfying a classification condition including the first pattern and not including the second pattern in the group Y. The evaluation value generation means 130 also computes 1 as a second argument number which the number of objects satisfying this classification condition in the group N. The evaluation value generation means 130 generates, on the basis of these argument numbers, an evaluation value by a chi-square test or the like. If the measure of classification indicated by the evaluation value is higher than the reference measure, the classification factor detection apparatus 10 can output the corresponding classification condition as a suitable factor of classification.

In the object database 100, the molecular structures of the chemical materials are stored as graph-structured data. The constituent addition means 150 adds one after another apexes, sides or subgraphs which are combinations of apexes and sides in the graph-structured data for generation of evaluation values. Thus, the classification factor detection apparatus 10 can suitably determine a factor of classification even in data in a format difficult to analyze, e.g., graph-structured data as well as in data in a format relatively easy to analyze, e.g., stored in a table, lattice-structured data, a typical log and the like.

FIG. 3 shows the flow of operation of the classification factor detection apparatus 10. The first selection means 110 selects an empty set as a first pattern (S300). The second selection means 120 selects an empty set as a second pattern (S310). The evaluation value generation means 130 performs processing for generating an evaluation value (S320). In processing for generating evaluation values, the constituent addition means 150 adds one after another constituents to the first pattern and/or the second pattern, and the evaluation value generation means 130 generated an evaluation value each time addition processing is performed. Details of the operation will be described with reference to FIGS. 4 to 6.

When the measure indicated by the evaluation value generated in S320 exceeds the predetermined reference measure, the classification factor output means 180 performs processing for outputting as a factor of classification the first pattern and the second pattern for which the evaluation value has been generated (S330). Alternatively, the classification factor output means 180 may output as a factor of classification the first pattern and the second pattern for which the evaluation value corresponding to the maximum of the measures indicated by the evaluation values generated by the evaluation value generation means 130 has been generated. In this case, a classification condition can be output with respect to the highest measure in the evaluation values generated by the evaluation value generation means 130.

For further instance, the classification factor output means 180 may output as a factor of classification a classification condition corresponding to each of a predetermined number of evaluation values determined in advance in descending order of measure in a plurality of evaluation values generated by the evaluation value generation means 130 and indicating measures exceeding the reference measure. In this case, even if a multiplicity of evaluation values exceeding the reference measure are generated, the classification factor output means 180 may select and output the predetermined number of evaluation values from the multiplicity of evaluation values.

FIG. 4 shows details of the operation flow in S320 shown in FIG. 3. FIG. 5 shows an operation flow following FIG. 4. FIG. 6 shows an operation flow following FIG. 5. The evaluation value generation means 130 computes, on the basis of the classification condition determined by the first pattern and the second pattern, a first argument number which is the number of objects satisfying the classification condition in the first group, and a second argument number which the number of objects satisfying the classification condition in the second group. The evaluation value generation means 130 then generates, on the basis of the first argument number and the second argument number, an evaluation value of the measure of classification of the plurality of objects under the classification condition (S400).

More specifically, the evaluation value generation means 130 generates, as an evaluation value, a chi-square test value indicating the deviation of a probability distribution of the objects satisfying the classification condition based on the first pattern and the second pattern from a probability distribution of the objects satisfying a classification condition of a correlation equal to or lower than a predetermined value with the classification results. Alternatively, the evaluation value generation means 130 may generate, as an evaluation value determined by an evaluation function, a value based on an entropy value indicating the uniformity of the first argument number and the second argument number, or may generate a Gini's coefficient value indicating the magnitude of the difference between the first argument number and the second argument number. For example, since the entropy value is a value indicating the uniformity of the first argument number and the second argument number, the evaluation value generation means 130 generates as an evaluation value a value which decreases according to the increase in the entropy value and increases according to the reduction in the entropy value.

When the measure indicated by the evaluation value generated by the evaluation value generation means 130 exceeds the reference measure stored in the reference measure storage means 160, the reference measure updating means 170 updates the reference measure by storing the measure indicated by the evaluation value as the reference measure in the reference measure storage means 160 while relating the measure to the first pattern and the second pattern at the time of generation of the evaluation value (S410).

Subsequently, the upper limit value estimation means 140 generates an upper limit value of the evaluation value in a possible region for the first argument number and the second argument number when one of the constituents is added to the first pattern and the second pattern (S420).

If the measure indicated by the upper limit value is equal to or lower than the reference measure (S430: NO) or if all the constituents selectable as the first pattern or the second pattern have already been selected (S440: YES), the classification factor detection apparatus 10 terminates the processing shown as S320.

If the measure indicated by the upper limit value is higher than the reference measure (S430: YES) and if some of the constituents selectable as the first pattern or the second pattern have not been selected (S440: NO), the classification factor detection apparatus 10 repeats processing described below with respect to each of unevaluated constituents which are constituents not included in the second pattern in the plurality of constituents belonging to some of the plurality of objects (S500).

The constituent addition means 150 first sends an instruction to the second selection means 120 to perform the first processing for adding the unevaluated constituent to the second pattern (S510). Receiving this instruction, the second selection means 120 generates a constituent-added second pattern by adding the unevaluated constituent (S520).

The evaluation value generation means 130 recursively performs the processing for generating an evaluation value by setting the first pattern and the constituent-added as new first and second patterns (S320). In a concrete example of a method for implementation of this recursive processing, the processing in S320 is realized by the function of a program in a predetermined programming language. In this case, the classification factor detection apparatus 10 inputs information on the first pattern and the constituent-added second pattern to the function as an argument by pass-by-value to use the information as new first and second patterns in the processing in S320.

Thus, the evaluation value generation means 130 can generate an evaluation value with respect to the new first and second patterns and can generate an evaluation value in the case of further adding the unevaluated constituent to the new first and second patterns.

The classification factor detection apparatus 10 repeats the above-described processing with respect to each of the unevaluated constituents (S530). The constituent addition means 150 can perform the first addition processing for generating constituent-added second patterns by adding each of the unevaluated constituents to the second pattern, and the evaluation value generation means 130 can generate an evaluation value with respect to each of the constituent-added second patterns.

Subsequently, the constituent addition means 150 makes a determination as to whether or not the first pattern and the second pattern are identical to each other (S600). If the first pattern and the second pattern are not identical to each other (S600: NO), the classification factor detection apparatus 10 terminates the processing shown as S320.

If the first pattern and the second pattern are identical to each other (S600: YES), the classification factor detection apparatus 10 further repeats processing described below with respect to each of the unevaluated constituents (S610). The constituent addition means 150 first sends instructions to the first selection means 110 and the second selection means 120 to perform the second addition processing for adding the unevaluated constituent to each of the first pattern and the second pattern (S620).

Advantageously, the constituent addition means 150 determines in advance the order in which the unevaluated constituents are added in order to prevent duplication of evaluation values with respect to the same classification condition. For instance, in a case where the objects are constituent A, constituent B, constituent C or a combination of these, the constituent addition means 150 adds constituent A, constituent B and constituent C in this order and does not perform addition processing by adding the constituents in the reverse order, thus preventing duplication of evaluation values as between the case in which constituent A and constituent B are added in this order and the case in which constituent B and constituent A are added in this order.

Receiving the instruction from the constituent addition means 150, the first selection means 110 generates a constituent-added first pattern by adding the unevaluated constituent to the first pattern (S630). Further, the second selection means 120 generates a constituent-added second pattern by adding the unevaluated constituent to the second pattern (S640).

The evaluation value generation means 130 recursively performs processing for generating an evaluation value by setting the constituent-added first pattern and the constituent-added second pattern as new first and second patterns (S320).

The classification factor detection apparatus 10 repeats the above-described processing with respect to each of the unevaluated constituents (S650) to complete the processing shown as S320. The constituent addition means 150 can perform the second addition processing for generating constituent-added first patterns and constituent-added second patterns by adding each of the unevaluated constituents to the first pattern and the second pattern in the case where the first pattern and the second pattern are identical to each other.

As described above with reference to the figures, the first selection means 110 and the second selection means 120 select empty sets as the first pattern and the second pattern. The constituent addition means 150 adds the unevaluated constituents to the first pattern and the second pattern one after another. The evaluation value generation means 130 generates an evaluation value with respect to each of the combination of the first pattern and the second pattern. The upper limit value estimation means 140 generates an upper limit value of the evaluation value when one of the constituents is added to the patterns. If the measure indicated by the upper limit value is equal to or lower than the desired reference measure, the upper limit value estimation means 140 stops the constituent addition processing. In this manner, the classification factor detection apparatus 10 can reduce the number of classification conditions to be evaluated, thereby reducing the search time.

FIG. 7 shows a table in which the data shown in FIG. 2 is classified. This figure shows details of the numbers of objects stored in the object database 100. For the description of this figure, it is assumed that the number of objects including the first pattern in the plurality of objects classified into the first group is a; the number of objects including the second pattern in the objects classified into the first group is b; the number of objects including the first pattern in the plurality of objects classified into the second group is c; and the number of objects including the second pattern in the objects classified into the second group is d.

The first argument number, i.e., the number of objects satisfying a classification condition including the first pattern $P_1$ but not including the second pattern $P_2$ in the class Y corresponding to the first group is (a–c). Also, the second argument number, i.e., the number of objects satisfying this classification condition in the class N corresponding to the second group is (b–d).

The total number of objects included in the class Y is y, and the total number of objects included in the class N is n. Accordingly, the total number of objects stored in the object database 100 is (y+n).

In this figure, the first argument number is indicated by symbol (1). The second argument number is indicated by symbol (2). The number of objects not satisfying the classification condition in the class Y is indicated by symbol (3). The number of objects not satisfying the classification condition in the class N is indicated by symbol (4).

Also, the total number of objects stored in the object database 100 and satisfying the classification condition is indicated by symbol (5). The total number of objects stored in the object database 100 and not satisfying the classification condition is indicated by symbol (6). Satisfying the classification condition is indicated by symbol (7). Not satisfying the classification condition is indicated by symbol (8). The total number of objects included in the class Y is indicated by symbol (9). The total number of objects included in the class N is indicated by symbol (10).

$$O_{IC} \quad (1)$$

$$O_{I\overline{C}} \quad (2)$$

$$O_{\overline{I}C} \quad (3)$$

$$O_{\overline{I}\overline{C}} \quad (4)$$

$$O_I \quad (5)$$

$$O_{\overline{I}} \quad (6)$$

$$P_1\overline{P}_2 \quad (7)$$

$$\overline{P_1\overline{P}_2} \quad (8)$$

$$O_C \quad (9)$$

$$O_{\overline{C}} \quad (10)$$

FIG. 8(*a*) shows an evaluation value generated by the evaluation number generation means 130. In this figure, the abscissa represents the first argument number and the ordinate represents the second argument number. The axis in the height direction represents a chi-square test value determined according to the first argument number and the first argument number. The evaluation value generation means 130 generates an evaluation value 800, which is a chi-square test value, when the first argument number is (a–c) and when the second argument number is (b–d).

The evaluation value generation means 130 generates, as an evaluation value and as a chi-square test value, a value determined by a downwardly convex evaluation function (a curved surface indicated by the solid line in the figure) with respect to each of the first argument number and the second argument number when one of the constituents is added to the first pattern and/or the second pattern. More specifically, the evaluation value generation means 130 generates an evaluation value by the following function (11) determining the value according to the first argument number and the second argument number.

$$chi(P_1\overline{P}_2) = f(O_{IC}, O_{I\overline{C}}) \quad (11)$$

$$= \frac{\{(O_{IC} + O_{I\overline{C}})y - O_{IC}(y+n)\}^2 (y+n)}{yn(O_{IC} + O_{I\overline{C}})(y + n - O_{IC} + O_{I\overline{C}})}$$

The process of derivation of the function (11) will be described. A probability distribution of the objects in a case where there is no correlation with the classification results is $E_{ij}$ determined by equation (12).

$$E_{ij} = (y + n) \times \frac{O_i}{y+n} \times \frac{O_j}{y+n} \quad (12)$$

The deviation of the probability distribution of the objects satisfying the classification condition based on the first pattern and the second pattern with respect to the case where there is no correlation with the classification results is determined by equation (13) on the basis of a chi-square definition formula.

$$chi(P_1\overline{P}_2) = \sum_{i \in \{I,\overline{I}\}, i \in \{C,\overline{C}\}} \frac{(O_{ij} - E_{ij})^2}{E_{ij}} \quad (13)$$

Function (11) is derived by substituting equation (12) in equation (13). In this embodiment, the chi-square test value indicating the deviation of the probability distribution of the objects satisfying the classification condition based on the first pattern and the second pattern from the probability distribution in the case where there is no correlation with the classification results is generated as an evaluation value. Alternatively, the evaluation value generation means 130 may generate as an evaluation value a chi-square test value indicating the deviation of the probability distribution of the objects satisfying the classification condition based on the first pattern and the second pattern from a probability distribution in a case where the correlation with the classification results is equal to or lower than a predetermined value. That is, the evaluation value generated by the evaluation value generation means 130 is not limited to the value determined by equation (11); a value indicating the measure of classification of the objects under a classification condition may suffice as the evaluation value.

For example, the function for determining the evaluation value generated by the evaluation value generation means 130 is not limited to the downwardly convex function based on the first argument number and the second argument number. For example, the evaluation value generation means 130 may generate a value determined by an evaluation function which determines a value with respect to each of the first argument number and the second argument number, and the maximum of which corresponds to one of end points in a possible region for the first argument number and the second argument number.

FIG. 8(*b*) is a diagram for explaining the upper limit value in a case where one of the constituents is added to the first pattern. When $P_1$ is expanded, that is, when the constituent addition means 150 adds one of the constituents to the first pattern, the set of constituents contained in the first pattern is increased and, therefore, the number of objects including the first pattern is reduced. Therefore, when $P_1$ is expanded, the first argument number is equal to or larger than 0 and equal to or smaller than a irrespective of the contents of the second pattern. Similarly, the second argument number is equal to or larger than 0 and equal to or smaller than b. For example, the evaluation value generation means 130 generates an evaluation value 830 when one of the constituents is added to the first pattern.

Consequently, the upper limit value when one of the constituents is added to the first pattern corresponds to the maximum of the values of the evaluation function at the plurality of end points in the region in which the first argument number is equal to or larger than 0 and equal to or smaller than a and the second argument number is equal to or larger than 0 and equal to or smaller than b. For example, if the evaluation value is a chi-square test value, the upper limit value is the maximum value of the end points corresponding to the case where each of the first argument number and the second argument number is 0 (equation (14)).

$$u_1(P_1\overline{P}_2)=\max\{f(a, 0), f(0, b)\} \quad (14)$$

Each of the ends point in the possible region for the first argument number and the second argument number is a point which is located out of the region when the first argument number or the second argument number is increased or reduced. For example, in a case where the possible region for the first argument number and the second argument number is expressed by a rectangle, the end points are points on the apexes or sides of the rectangle.

FIG. 8(c) is a diagram for explaining the upper limit value in a case where one of the constituents is added to the second pattern. $P_1 \subset P_2$ denotes that the first pattern is a subset, a subtree or a subgraph of the second pattern. In a case where $P_2$ is expanded under the condition $P_1 \subset P_2$, that is, one of the constituents is added to the second pattern, the set of constituents contained in the second pattern is increased and, therefore, the number of objects satisfying the classification condition including the first pattern but not including the second pattern is increased. Therefore, when $P_2$ is expanded under the condition $P_1 \subset P_2$, the first argument number is equal to or larger than a–c and equal to or smaller than a irrespective of the contents of the second pattern. Similarly, the second argument number is equal to or larger than b–d and equal to or smaller than b. For example, the evaluation value generation means 130 generates an evaluation value 840 when one of the constituents is added to the second pattern.

Consequently, the upper limit value when one of the constituents is added to the second pattern corresponds to the maximum of the values of the evaluation function at the plurality of end points in the region in which the first argument number is equal to or larger than a–c and equal to or smaller than a and the second argument number is equal to or larger than b–d and equal to or smaller than b. For example, if the evaluation value is a chi-square test value, the upper limit value is the maximum of f(a–c, b) which is the chi-square test value in the case where the number of the objects including the second pattern in the second group is 0 and f(a, b–d) which is the chi-square test value in the case where the number of the objects including the first pattern in the second group is 0 (equation (15)).

$$u_2(P_1\overline{P}_2)=\max\{f(a-c, b), f(a, b-d)\} \quad (15)$$

The constituent addition means 150 repeats the first and second addition processings for generation of evaluation values with respect to all the combinations of the first pattern and the second pattern selectable as classification conditions. More specifically, the constituent addition means 150 performs the first and second addition processings when the first pattern and the second patterns are identical to each other, and performs the second addition processing when the first pattern and the second pattern are not identical to each other.

When the constituent addition means 150 performs the second addition processing, the upper limit value of the evaluation value is a value determined by $U_1$ shown by equation (14). On the other hand, when the constituent addition means 150 performs the first addition processing, the upper limit value of the evaluation value is a value determined by $U_2$ shown by equation (15). However, since the first pattern and the second pattern are identical to each other when the constituent addition means 150 performs the second addition processing, the number a, which is the number of objects including the first pattern in the first group, and the number c, which is the number of objects including the second pattern in the first group are equal to each other. Similarly, the number b, which is the number of objects including the first pattern in the second group, and the number d, which is the number of objects including the second pattern in the second group are equal to each other. In this case, $U_1=U_2$.

Therefore, the upper limit value estimation means 140 generates the maximum of f(a–c, b) and f(a, b–d) as the upper limit value of the chi-square test value when one of the constituents is added to each of the first pattern and the second pattern or to the second pattern. According to the example shown in the figure, the upper limit value estimation means 140 generates the maximum of the upper limit candidate value 810 and the upper limit candidate value 820 as the upper limit value.

As described above with reference to the figure, the evaluation value generation means 130 generates as an evaluation value a value determined by the downwardly convex function indicated by the solid line in FIG. 8(a) when one of the constituents is added to each of the first pattern and the second pattern or to the second pattern. The possible region for the first argument number and the second argument number at the time of addition processing performed by the constituent addition means 150 is determined.

Consequently, the upper limit value estimation means 140 can generate the upper limit value of the evaluation value when one of the constituents is added to the first pattern and/or the second pattern.

FIG. 9 shows an example of a search tree showing the order of search for a classification condition satisfying the reference measure. This figure shows the order in which evaluation values are generated in a case where each of the plurality of objects is constituent A, constituent B, constituent C or a combination of these.

First, the first selection means 110 selects an empty set as a first pattern and the second selection means 120 selects an empty set as a second pattern (S900). The constituent addition means 150 adds one after another the unevaluated constituents to the first pattern and the second pattern for generation of evaluation values with respect to all the selectable combinations of the first pattern and the second pattern.

More specifically, the evaluation value generation means 130 generates evaluation values with respect to the case where each of the first pattern and the second pattern includes constituent A (S905), the case where constituent B is added to the second pattern in S905 (S910), the case where constituent C is added to the second pattern in S910 (S915), the case where constituent C is added to the second pattern in S905 (S920), the case where constituent B is added to the first pattern and the second pattern in S905 (S925), the case where constituent C is added to the second pattern in S925 (S930), and the case where constituent C is added to the first pattern and the second pattern in S925 (S935). Similarly, the evaluation value generation means 130 generate evaluation values in S940 to S995 by the first addition processing and the second addition processing.

When the evaluation value generation means 130 generates the evaluation value in each of the above-described steps, the upper limit value estimation means 140 generates the upper limit value of the evaluation value when one of the constituents is added to the first pattern and/or the second pattern. If the measure indicated by the upper limit value is equal to or lower than the reference measure, the constituent addition means 150 stops constituent addition. For example, if the measure indicated by the upper limit value generated by the upper limit value estimation means 140 is equal to or lower than the reference measure in S950 of the figure, the constituent addition means 150 stops constituent addition. That is, the evaluation value generation means 130 moves the process to S950 without performing processing from S910 to S945.

If the evaluation value generation means 130 generates evaluation values with respect to all the selectable combinations of the first pattern and the second pattern, a considerably long computation time is required due to the large number of combinations. In contrast, in this embodiment, search tree trimming processing is performed in such a manner that the upper limit value estimation means 140 generates the upper limit value for further constituent addition each time one of the constituents is added to the first pattern and/or the second pattern, and the addition processing is stopped when the measure indicated by the upper limit value is equal to or lower than the reference measure. Thus, the evaluation value can be generated only when there is a possibility of the measure indicated by the evaluation value being higher than the reference measure. The amount of processing for generation of evaluation values is thereby reduced to shorten the computation time.

According to the example shown in the figure, the classification factor detection apparatus 10 performs a priority search in such a manner that processing for generating an evaluation value is repeated by adding the unevaluated constituents one after another. Alternatively, the classification factor detection apparatus 10 may perform a width priority search by repeating processing for adding each of the unevaluated constituents. That is, the evaluation value generation order shown in the figure is only an example and the constituent addition means 150 may add the unexamined evaluation constituent to the first pattern and/or the second pattern to enable the evaluation value generation means 130 to generate evaluation values with respect to all the combinations of constituents which the first pattern and the second pattern can contain.

FIG. 10($a$) shows an example of a chemical material recognized as having pharmacological activity through predetermined analysis. FIG. 10($b$) shows an example of a chemical material relating to that shown in FIG. 10($a$). FIG. 10($c$) shows an example of a structure detected as a pattern having pharmacological activity by a method different from that in this embodiment. Azidothymidine shown in FIG. 10($a$) and having a structure similar to that of thymine shown in FIG. 10($b$) is known as an anti-HIV (human immunodeficiency virus) drug through cellular biological analysis.

HIV enters a CD4 cell which plays a dominant role in the immune system. HIV then proliferates and destroys the cell. When a CD4 cell is infected with HIV, RNA of HIV is converted into double-strand DNA by a reverse transcriptase to be incorporated in host chromosomes. If this function of double-strand DNA can be limited, the activity of HIV can be reduced.

However, since the ability of DNA incorporated in host chromosomes is concealed in the ability of the host cell, it is difficult to reduce the activity of HIV by this method. On the other hand, a method of reducing the activity of HIV by limiting the function of reverse transcriptase having no action on a healthy host cell is known. For example, azidothymidine shown in FIG. 10($a$) is known as a reverse transcription inhibitor capable of limiting the function of reverse transcriptase. More specifically, azidothymidine is added to a DNA strand by coupling to a certain portion of reverse transcriptase while the DNA strand is extending. Since azidothymidine has no OH group at an end corresponding to the position 3', it is capable of inhibiting further synthesis of the DNA strand (See non-patent document 1).

An apparatus relating to some other data mining method detects the pattern shown in Figure (c) as a pattern having pharmacological activity. For example, an apparatus relating to the method disclosed in non-patent document 10 detects the pattern shown in Figure (c) as a pattern having pharmacological activity because the chi-square test value of the pattern shown in FIG. 10($c$) is 4979.5, higher than the reference value.

Since pattern shown in FIG. 10($c$) is a pattern included in azidothymidine shown in FIG. 10($a$), this apparatus can suitably detect the pattern having pharmacological activity. However, there are many chemical materials including the pattern shown in FIG. 10($c$). Therefore it is possible of the apparatus detecting some other chemical materials having a low pharmacological activity as the pattern having pharmacological effect. In contrast, the classification factor detection apparatus 10 in this embodiment is capable of detecting a set satisfying a predetermined condition, as described below with reference to FIGS. 11 and 12.

FIG. 11($a$) shows an example of a first pattern output as a factor of classification by the classification factor detection apparatus 10. FIG. 11($b$) shows an example of a second pattern output as a factor of classification by the classification factor detection apparatus 10. A concrete example of processing for outputting this factor of classification will be described below. In this example, the objects are chemical materials and the constituents are a plurality of elements or chemical bonds of the elements. The plurality of chemical materials are classified into two groups on the basis of the results of determination by experiment as to whether each chemical material has a predetermined effect as a drug.

More specifically, 42687 chemical materials in HIV data (See non-patent document 6) used in the example shown in these figures are classified by experiment into a group CA recognized as having activity on HIV and a group CI not recognized as having any activity on HIV.

The first selection means 110 selects as a first pattern a set of at least one element and a bond between elements in the elements of one of the plurality of chemical materials or bonds between the elements, and the second selection means 120 selects as a second pattern a set of elements or bonds between elements formed by adding at least one element or a bond between elements to the first pattern. For example, each of the first selection means 110 and the second selection means 120 selects a set of apexes, sides, or apexes and sides of graphs as each of the first pattern and the second pattern from data in which the elements correspond to the apexes of the graphs and in which the bonds between the elements correspond to the sides of the graphs.

More specifically, there are 66 kinds of apexes corresponding to carbon, nitrogen, oxygen, etc. Elements having an aromatic bond and elements having no aromatic bond are discriminated from each other and are treated as different apexes even if they are of the same kind. Also, there are four kinds of sides for a single bond, a double bond, a triple bond and an aromatic bond.

The evaluation value generation means 130 generates an evaluation value according to a first argument number which is the number of chemical materials satisfying a classification condition in the plurality of chemical materials classified into the group CA and a second argument number which is the number of chemical materials satisfying the classification condition in the chemical materials classified into the group CI. For example, the evaluation value generation means 130 generates 5394 as a chi-square test value based on the first group shown in FIG. 11(a) and the second group shown in FIG. 11(b).

When the measure indicated by the evaluation value exceeds the reference measure, the classification factor output means 180 outputs the set of chemical materials in each of the first pattern and the second pattern as a factor of classification of the chemical materials having the predetermined effect. For example, the classification factor output means 180 outputs each of the first group shown in FIG. 11(a) and the second group shown in FIG. 11(b) as a factor of classification because the measure indicated by the chi-square test value 5394.

Thus, the classification factor detection apparatus 10 can detect a chemical material including the constituent shown in FIG. 11(a) and not including the constituent shown in FIG. 11(b) as a chemical material having pharmacological activity. In this way, the classification factor detection apparatus 10 can suitably detect not only the pattern having the pharmacological effect but also the pattern which is a cause of a reduction in the pharmacological effect. In particular, even though the degree of support for the second pattern is extremely low, 0.02%, the classification factor detection apparatus 10 can suitably detect the pattern as a cause of a reduction in the pharmacological effect.

FIG. 12(a) shows another example of the first pattern output as a factor of classification by the classification factor detection apparatus 10. FIG. 12(b) shows another example of the second pattern output as a factor of classification by the classification factor detection apparatus 10. The classification factor output means 180 may output a plurality of evaluation values having measures higher than the reference measure. For example, the classification factor output means 180 may output, as factors of classification, classification conditions corresponding to a certain number of evaluation values determined in advance in descending order of measure in a plurality of evaluation values indicating measures exceeding the reference measure.

The classification factor output means 180 outputs the first pattern shown in FIG. 12(a) and the second pattern shown in FIG. 12(b) as patterns corresponding to evaluation values having measures higher than the reference measure as in the case of the classification conditions shown in FIGS. 11(a) and 11(b). Thus, the classification factor detection apparatus 10 may output as classification factors a plurality of combinations of patterns having a pharmacological effect and patterns each of which is a cause of a reduction in the pharmacological effect.

FIG. 13 shows an example of outputting of a factor for classification of news items. In this example, the objects are sentences representing the contents of news items and the constituents are words and phrases in the sentences. In the constituent words and phrases, at least one letter or word may form one constituent. The news items shown in the figure are classified into a domestic economic news group Y and an international economic news group N through analysis of the genres of news items performed by news writers or news editors.

The first selection means 110 selects as a first pattern a set of at least one word or phrase in the plurality of words and phrases classified into the first group. The second selection means 120 selects as a second pattern a set of words and/or phrases formed by adding at least one word or phrase to the first pattern.

The evaluation value generation means 130 generates an evaluation value according to the number of sentences satisfying a classification condition in the plurality of words and phrases classified into the first group and the number of sentences satisfying the classification condition in the sentences classified into the second group.

When the measure indicated by the evaluation value exceeds the reference measure, the classification factor output means 180 outputs the set of words and/or phrases in each of the first pattern and the second pattern as a factor of classification of the plurality of sentences into the predetermined genres. For example, the classification factor output means 180 detects a word "price" as the first pattern, detects the word "price" and a word "international", and outputs these pattern sets as a factor of classification of domestic economic news.

Thus, the objects from which the classification factor detection apparatus 10 in this embodiment detects a factor are not limited to chemical materials; the classification factor detection apparatus 10 may detect a factor for classification of sentences forming news items. Consequently, even news items newly written can be speedily classified into suitable genres by using the classification factor detection apparatus 10.

In the example shown in the figure, the classification factor detection apparatus 10 detects a set of words and/or phrases as the first pattern or the second pattern. The classification factor detection apparatus 10 may also detect, as the first pattern or the second pattern, a result of syntactic analysis which is a combination of a word modification relationship, a paragraph formed by words and phrases, the structure of sentences, etc. For example, the classification factor detection apparatus 10 may detect a factor of classification on the basis of data describing a syntactic analysis result in graph- or tree-structured form.

FIG. 14 shows an example of outputting of a factor for classification of Web page browse records. In this example, the objects are records of browses on a World Wide Web site and the constituents are Web pages browsed and sequence information indicating a browse sequence. A plurality of browse records are classified into two groups by processing performed as a result of browsing. For example, a plurality of browse records are classified into a group Y of records showing cases of purchase and sale of commodities and a group N of records showing cases without purchase and sale of any commodities according to whether or not purchase and sale of commodities have been performed on Web pages.

The first selection means 110 selects as a first pattern at least one of Web pages and sequence information in one of the browse records, and the second selection means 120 selects a second pattern formed by adding at least one Web page or sequence information to the first pattern.

The evaluation value generation means 130 generates an evaluation value according to the number of browse records satisfying a classification condition in the plurality of browse records classified into the first group and the number of browse records satisfying the classification condition in the browse records classified into the second group.

When the measure indicated by the evaluation value exceeds the reference measure, the classification factor output means 180 outputs the set of the Web page and the browse sequence in each of the first pattern and the second pattern as a factor of classification according to whether or not purchase and sale of a commodity are performed in the course of or as a result of browsing. For example, the classification factor output means 180 detects a Web page "Purchase Confirmation" as the first pattern, detects Web pages "Purchase Confirmation" and "Commodity Performance" as the second pattern, and outputs these pattern sets as a factor for classification of the browse records showing cases of purchase and sale of commodities.

Thus, according to this example, the classification factor detection apparatus 10 can perform processing on Web page browse records and suitably detect and output a factor of classification of the browse records. Therefore, the classification factor detection apparatus 10 can support marketing, etc., in commodity trading using the World Wide Web system.

FIG. 15 shows an example of a hardware configuration of the classification factor detection apparatus 10. The classification factor detection apparatus 10 has a CPU peripheral section having a CPU 1000, a RAM 1020, a graphic controller 1075 and a display device 1080 connected to each other by a host controller 1082, an input/output section having a communication interface 1030, a hard disk drive 1040 and a CD-ROM drive 1060 connected to the host controller 1082 by an input/output controller 1084, and a legacy input/output section having a ROM 1010, a flexible disk drive 1050 and an input/output chip 1070 connected to the input/output controller 1084.

The host controller 1082 connects the RAM 1020, and the CPU 1000 and the graphic controller 1075, which access the RAM 1020 at a high transfer rate. The CPU 1000 operates on the basis of programs stored in the ROM 1010 and the RAM 1020, and controls each component. The graphic controller 1075 obtains image data generated by the CPU 1000, etc., on a frame buffer provided in the RAM 1020, and displays the image data on the display device 1080. Alternatively, the graphic controller 1075 may contain therein a frame buffer for storing image data generated by the CPU 1000, etc.

The input/output controller 1084 connects the host controller 1082, the communication interface 1030, which is an input/output device of a comparatively high speed, the hard disk drive 1040 and the CD-ROM drive 1060. The communication interface 1030 performs communication with external units through a network such as a fiber channel.

The hard disk drive 1040 stores programs and data used by the classification factor detection apparatus 10. The CD-ROM drive 1060 reads a program or data from a CD-ROM 1095 and provides the read program or data to the input/output chip 1070 via the RAM 1020.

To the input/output controller 1084 are connected the ROM 1010 and input/output devices of a comparatively low speed, i.e., the flexible disk drive 1050 and the input/output chip 1070 or the like. The ROM 1010 stores a boot program executed by the CPU 1000 at the time of startup of the classification factor detection apparatus 10, and programs, etc., dependent on the hardware of the classification factor detection apparatus 10. The flexible disk drive 1050 reads a program or data from a flexible disk 1090 and provides the read program or data to the input/output chip 1070 via the RAM 1020. The input/output chip 1070 connects the flexible disk 1090 and various input/output devices, for example, through a parallel port, a serial port, a keyboard port, a mouse port, etc.

A program provided to the classification factor detection apparatus 10 is provided by a user in a state of being stored on a recording medium, such as the flexible disk 1090, the CD-ROM 1095, or an IC card. The program is read out from the recording medium, installed in the classification factor detection apparatus 10 via the input/output chip 1070 and/or the input/output controller 1084, and executed in the classification factor detection apparatus 10.

A program installed and executed in the classification factor detection apparatus 10 includes a first selection module, a second selection module, an evaluation value generation module, an upper limit value estimation module, a constituent addition module, a reference measure storage module, a reference measure updating module, and a classification factor output module. Operations which the classification factor detection apparatus 10 is made by the modules to perform are the same as the operations of the corresponding components in the classification factor detection apparatus 10 described above with reference to FIGS. 1 to 14. Therefore, description of the operations will not be repeated.

The above-described program or modules may be stored on an external storage medium. As the recording medium, an optical recording medium such as a DVD or a PD, a magneto-optic recording medium such as an MD, a tape medium, a semiconductor memory such as an IC card, or the like can be used as well the flexible disk 1090 and the CD-ROM 1095. Also, a storage device such as a hard disk or a RAM provided in a server system connected to a special-purpose communication network or the Internet may be used as the recording medium to provide the program to the classification factor detection apparatus 10 via the network.

As described above with respect to the embodiment, the classification factor detection apparatus 10 detects, with respect to the results of classification into two groups of a plurality of objects each constituted by a plurality of constituents through analysis as to whether or not each object has a predetermined characteristic, a set of some of the constituents as a factor of the classification.

More specifically, the classification factor detection apparatus 10 can detect, as a factor of classification, not only a condition as to whether or not a predetermined pattern is included but also a classification condition including a first pattern but not including a second pattern. In this manner, a suitable classification factor, e.g., a chemical structure having a predetermined effect as a drug and having no considerable side effect can be detected in various fields of application.

Also, the classification factor detection apparatus 10 generates a measure of classification by adding the constituents to the first pattern and/or the second pattern one after another. The classification factor detection apparatus 10 generates an upper limit value of the evaluation value with respect to further addition of one of the constituents to the first pattern and/or the second pattern. If the upper limit value is lower than the desired measure, the classification factor detection apparatus 10 stops further addition processing. Thus, the evaluation value can be generated only with respect to a classification condition ensuring a possibility of the evaluation value exceeding the upper limit value. A reduction in computation processing time can be achieved in this way.

The present invention has been explained by using the embodiment thereof. However, the technical scope of the present invention is not limited to the scope described above with respect to the embodiment. It is apparent to those skilled in the art that various modifications and changes can be made in the above-described embodiment. It is apparent from the description in the appended claims that forms having such changes or modifications are also included in the technical scope of the present invention.

According to the above-described embodiment, a classification factor detection apparatus, a classification factor detection method, a program and a recording medium described in items below are realized.

(Item 1) A classification factor detection apparatus which detects, with respect to the results of classification into two groups of a plurality of objects each constituted by a plurality of constituents through analysis as to whether or not each object has a predetermined characteristic, a set of some of the constituents as a factor of the classification, the apparatus having first selection means of selecting a first pattern which is a set of at least one of the plurality of constituents of one of the plurality of objects, second selection means of selecting, from the plurality of constituents in one of the plurality of objects, a second pattern formed of the first pattern and at least one of the constituents added to the first pattern, evaluation value generation means of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, and classification factor output means of outputting the constituents in each of the first pattern and the second pattern as a factor of classification when the measure indicated by the evaluation value exceeds a reference measure determined in advance.

(Item 2) The classification factor detection apparatus described in Item 1, wherein the evaluation value generation means generates as the evaluation value a value determined by a downwardly convex function with respect to each of a first argument number which is the number of objects satisfying the classification condition in the first group and a second argument number which is the number of objects satisfying the classification condition in the second group, the apparatus further having upper limit estimation means of generating, as an upper limit value of the evaluation value in a possible region for the first argument number and the second argument number when one of the constituents is added to the first pattern and/or the second pattern, the maximum of values of the evaluation function at a plurality of end points of the region, and constituent addition means of performing processing for adding the same constituent to each of the first pattern and the second pattern or processing for adding the constituent to the second pattern when the measure indicated by the upper limit value is higher than the reference measure, and wherein the evaluation value generation means further generates the evaluation value with respect to the first pattern and/or the second pattern to which one of the constituents has been added by the constituent addition means.

(Item 3) The classification factor detection apparatus described in Item 2, wherein the evaluation value generation means generates, as the evaluation value determined by the evaluation function, a chi-square test value representing the deviation of a probability distribution of the objects satisfying the classification condition based on the first pattern and the second pattern from a probability distribution of the objects satisfying a classification condition of a correlation equal to or lower than a predetermined value with the classification results.

(Item 4) The classification factor detection apparatus described in Item 3, wherein if the number of objects including the first pattern in the plurality of objects classified into the first group is a; the number of objects including the second pattern in the objects classified into the first group is b; the number of objects including the first pattern in the plurality of objects classified into the second group is c; and the number of objects including the second pattern in the objects classified into the second group is d, the evaluation value generation means generates, as the evaluation value, a value determined by f(a−c, b−d) which is the evaluation function generating the chi-square test value on the basis of (a−c) which is the first argument number and (b−d) which is the second argument number, and the upper limit value estimation means generates, as an upper limit value of the chi-square test value when one of the constituents is added to each of the first pattern and the second pattern or to the second pattern, the maximum of f(a−c, b) which is the chi-square test value in the case where the number of objects including the second pattern in the second group is 0 and f(a, b−d) which is the chi-square test value in the case where the number of objects including the first pattern in the second group is 0.

(Item 5) The classification factor detection apparatus described in Item 2, wherein the evaluation value generation means generates, as the evaluation value determined by the evaluation function, a value based on an entropy value indicating the uniformity of the first argument number and the second argument number.

(Item 6) The classification factor detection apparatus described in Item 2, wherein the evaluation value generation means generates, as the evaluation value determined by the evaluation function, Gini's coefficient value indicating the magnitude of the difference between the first argument number and the second argument number.

(Item 7) The classification factor detection apparatus described in Item 2, wherein the upper limit value estimation means generates an upper limit value of the evaluation value in the case of adding the same constituent to each of the first pattern and the second pattern and in the case of adding the constituent to the second pattern while maintaining the same contents of the first pattern each time the evaluation value is generated by the evaluation value generation means; when the measure indicated by the upper limit value is higher than the reference measure, the constituent addition means performs first addition processing for generating each of constituent-added second patterns formed by adding to the second pattern unevaluated constituents which are constituents not included in the second pattern in the plurality of constituents in one of the plurality of objects, and, if the first pattern and the second pattern are identical to each other, performs second addition processing for generating each of constituent-added first patterns and constituent-added second patterns formed by adding the unevaluated constituents to the first pattern and the second pattern; and the evaluation value generation means generates the evaluation value with respect to the constituent-added first pattern and the constituent-added second pattern after the first or second addition processing.

(Item 8) The classification factor detection apparatus described in Item 2, further having reference measure storage means of storing the reference measure, and reference measure updating means of storing, as the reference measure, in the reference measure storage means, the measure indicated by the evaluation value generated by the evaluation value generation means by relating the measure to the first pattern and the second pattern at the time of generation of the evaluation value if the measure indicated by the evaluation value exceeds the reference value, wherein the classification factor output means outputs, as a factor of classification, the first pattern and the second pattern stored in the reference measure storage means.

(Item 9) The classification factor detection apparatus described in Item 2, wherein the classification factor output means outputs, as a factor of classification, a classification condition corresponding to each of a predetermined number of evaluation values determined in advance in descending order of measure in a plurality of the evaluation values generated by the evaluation value generation means and indicating measures exceeding the reference measure.

(Item 10) The classification factor detection apparatus described in Item 1, wherein the evaluation value generation means generates as the evaluation value a value determined by an evaluation function which determines a value with respect to each of a first argument number which is the number of objects satisfying the classification condition in the first group and a second argument number which is the number of objects satisfying the classification condition in the second group, and the maximum of which corresponds to one of end points in a possible region for the first argument number and the second argument number, the apparatus further having upper limit estimation means of generating, as an upper limit value of the evaluation value in a possible region for the first argument number and the second argument number when one of the constituents is added to the first pattern and/or the second pattern, the maximum of values of the evaluation function at a plurality of end points of the region, and constituent addition means of performing processing for adding the same constituent to each of the first pattern and the second pattern or processing for adding the constituent to the second pattern when the measure indicated by the upper limit value is higher than the reference measure, and wherein the evaluation value generation means further generates the evaluation value with respect to the first pattern and/or the second pattern to which one of the constituents has been added by the constituent addition means.

(Item 11) The classification factor detection apparatus described in Item 1, wherein the objects are chemical materials in each of which a plurality of elements corresponding to the plurality of constituents bond chemically together; a plurality of the chemical materials are classified into two groups on the basis of the results of determination by experiment as to whether each chemical material has a predetermined effect as a drug; the first selection means selects as the first pattern a set of at least one element and a bond between elements in the elements of one of the plurality of chemical materials or bonds between the elements; the second selection means selects as the second pattern a set of elements or bonds between elements formed by adding at least one element or a bond between elements to the first pattern; the evaluation value generation means generates the evaluation value according to the number of chemical materials satisfying the classification condition in the plurality of chemical materials classified into the first group and the number of chemical materials satisfying the classification condition in the chemical materials classified into the second group; and, when the measure indicated by the evaluation value exceeds the reference measure, the classification factor output means outputs the set of chemical materials in each of the first pattern and the second pattern as a factor of classification of the chemical materials having the predetermined effect.

(Item 12) The classification factor detection apparatus described in Item 1, wherein the objects are sentences each formed of a plurality of words and/or phrases; a plurality of the sentences are classified into two groups according to genres indicating the contents of the sentences; the first selection means selects as the first pattern a set of at least one word or phrase in the words and phrases in one of the plurality of sentences; the second selection means selects as the second pattern a set of words and/or phrases formed by adding at least one word or phrase to the first pattern; the evaluation value generation means generates the evaluation value according to the number of sentences satisfying the classification condition in the plurality of words and phrases classified into the first group and the number of sentences satisfying the classification condition in the sentences classified into the second group; and when the measure indicated by the evaluation value exceeds the reference measure, the classification factor output means outputs the set of words and/or phrases in each of the first pattern and the second pattern and second pattern as a factor of classification of the plurality of sentences into the predetermined genres.

(Item 13) The classification factor detection apparatus described in Item 1, wherein the objects are records of browses on a World Wide Web site; the constituents are Web pages browsed and sequence information indicating a browse sequence; a plurality of the browse records are classified into two groups by processing performed as a result of browsing; the first selection means selects as the first pattern at least one of the Web pages and sequence information in one of the browse records; the second selection means selects the second pattern formed by adding at least one of the Web pages or the sequence information to the first pattern; the evaluation value generation means generates the evaluation value according to the number of browse records satisfying the classification condition in the plurality of browse records classified into the first group and the number of browse records satisfying the classification condition in the browse records classified into the second group; and when the measure indicated by the evaluation value exceeds the reference measure, the classification factor output means outputs the set of the Web page and the browse sequence in each of the first pattern and the second pattern as a factor of classification according to the processing performed as a result of browsing.

(Item 14) The classification factor detection apparatus described in Item 13, wherein the plurality of browse records are classified into the two groups according to whether or not purchase and sale of commodities have been performed on the Web pages in the course of or as a result of browsing; and, when the measure indicated by the evaluation value exceeds the reference measure, the classification factor output means outputs the Web page and the browse sequence in each of the first pattern and the second pattern as a factor of classification according to whether or not purchase and sale of a commodity are performed in the course of or as a result of browsing.

(Item 15) A classification factor detection method in which, with respect to the results of classification into two groups of a plurality of objects each constituted by a plurality of constituents through analysis as to whether or not each object has a predetermined characteristic, a set of some of the constituents is detected as a factor of the classification by a computer, the method including, as steps performed by the computer, a first selection step of selecting a first pattern which is a set of at least one of the plurality of constituents of one of the plurality of objects, a second selection step of selecting, from the plurality of constituents in one of the plurality of objects, a second pattern formed of the first pattern and at least one of the constituents added to the first pattern, an evaluation value generation step of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, and a classification factor output step of outputting the constituents in each of the first pattern and the second pattern as a factor of classification when the measure indicated by the evaluation value exceeds a reference measure determined in advance.

(Item 16) The classification factor detection method described in Item 15, wherein, in the evaluation value generation step, the computer generates as the evaluation value a value determined by a downwardly convex function with respect to each of a first argument number which is the number of objects satisfying the classification condition in the first group and a second argument number which is the number of objects satisfying the classification condition in the second group, the method further including, as steps performed by the computer, an upper limit estimation step of generating, as an upper limit value of the evaluation value in a possible region for the first argument number and the second argument number when one of the constituents is added to the first pattern and/or the second pattern, the maximum of values of the evaluation function at a plurality of end points of the region, and a constituent addition step of performing processing for adding the same constituent to each of the first pattern and the second pattern or processing for adding the constituent to the second pattern when the measure indicated by the upper limit value is higher than the reference measure, and wherein, in the evaluation value generation step, the computer further generates the evaluation value with respect to the first pattern and/or the second pattern to which one of the constituents has been added in the constituent addition step.

(Item 17) A program for making a computer function as a classification factor detection apparatus which detects, with respect to the results of classification into two groups of a plurality of objects each constituted by a plurality of constituents through analysis as to whether or not each object has a predetermined characteristic, a set of some of the constituents as a factor of the classification, the program making the computer function as first selection means of selecting a first pattern which is a set of at least one of the plurality of constituents of one of the plurality of objects, second selection means of selecting, from the plurality of constituents in one of the plurality of objects, a second pattern formed of the first pattern and at least one of the constituents added to the first pattern, evaluation value generation means of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, and classification factor output means of outputting the constituents in each of the first pattern and the second pattern as a factor of classification when the measure indicated by the evaluation value exceeds a reference measure determined in advance.

(Item 18) The program described in Item 17, wherein the evaluation value generation means generates as the evaluation value a value determined by a downwardly convex function with respect to each of a first argument number which is the number of objects satisfying the classification condition in the first group and a second argument number which is the number of objects satisfying the classification condition in the second group, the program making the computer further function as upper limit estimation means of generating, as an upper limit value of the evaluation value in a possible region for the first argument number and the second argument number when one of the constituents is added to the first pattern and/or the second pattern, the maximum of values of the evaluation function at a plurality of end points of the region, and constituent addition means of performing processing for adding the same constituent to each of the first pattern and the second pattern or processing for adding the constituent to the second pattern when the measure indicated by the upper limit value is higher than the reference measure, and wherein the evaluation value generation means further generates the evaluation value with respect to the first pattern and/or the second pattern to which one of the constituents has been added by the constituent addition means.

(Item 19) A recording medium on which the program described in Item 17 or 18 is recorded.

Variations described for the present invention can be realized in any combination desirable for each particular application. Thus particular limitations, and/or embodiment enhancements described herein, which may have particular advantages to the particular application need not be used for all applications. Also, not all limitations need be implemented in methods, systems and/or apparatus including one or more concepts of the present invention.

The present invention can be realized in hardware, software, or a combination of hardware and software. A visualization tool according to the present invention can be realized in a centralized fashion in one computer system, or in a distributed fashion where different elements are spread across several interconnected computer systems. Any kind of computer system—or other apparatus adapted for carrying out the methods and/or functions described herein—is suitable. A typical combination of hardware and software could be a general purpose computer system with a computer program that, when being loaded and executed, controls the computer system such that it carries out the methods described herein. The present invention can also be embedded in a computer program product, which comprises all the features enabling the implementation of the methods described herein, and which—when loaded in a computer system—is able to carry out these methods.

Computer program means or computer program in the present context include any expression, in any language, code or notation, of a set of instructions intended to cause a system having an information processing capability to perform a particular function either directly or after conversion to another language, code or notation, and/or reproduction in a different material form.

Thus, the invention includes an article of manufacture which comprises a computer usable medium having computer readable program code means embodied therein for causing a function described above. The computer readable program code means in the article of manufacture comprises computer readable program code means for causing a computer to effect the steps of a method of this invention. Similarly, the present invention may be implemented as a computer program product comprising a computer usable medium having computer readable program code means embodied therein for causing a a function described above. The computer readable program code means in the computer program product comprising computer readable program code means for causing a computer to effect one or more functions of this invention. Furthermore, the present invention may be implemented as a program storage device readable by machine, tangibly embodying a program of instructions executable by the machine to perform method steps for causing one or more functions of this invention.

It is noted that the foregoing has outlined some of the more pertinent objects and embodiments of the present invention. This invention may be used for many applications. Thus, although the description is made for particular arrangements and methods, the intent and concept of the invention is suitable and applicable to other arrangements and applications. It will be clear to those skilled in the art that modifications to the disclosed embodiments can be effected without departing from the spirit and scope of the invention. It is noted that not all the necessary features of the invention are listed. Subcombinations of the features can constitute the present invention. The described embodiments ought to be construed to be merely illustrative of some of the more prominent features and applications of the invention. Other beneficial results can be realized by applying the disclosed invention in a different manner or modifying the invention in ways known to those familiar with the art.

What is claimed, is:

1. A classification factor detection apparatus which detects, with respect to the results of classification into two groups of a plurality of objects each constituted by a plurality of constituents through analysis as to whether or not each object has a predetermined characteristic, a set of some of the constituents as a factor of the classification, said apparatus comprising:

first selection means of selecting a first pattern which is a set of at least one of the plurality of constituents of one of the plurality of objects;

second selection means of selecting, from the plurality of constituents in one of the plurality of objects, a second pattern formed of the first pattern and at least one of the constituents added to the first pattern;

evaluation value generation means of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, wherein the evaluation value is a chi-square test value representing the deviation of a probability distribution of the objects satisfying the classification condition based on the first pattern and the second pattern from a probability distribution of the objects satisfying a classification condition of a correlation equal to or lower than a predetermined value with the classification results; and classification factor output means of outputting the constituents in each of the first pattern and the second pattern as a factor of classification when the measure indicated by the evaluation value exceeds a reference measure determined in advance.

2. The classification factor detection apparatus according to claim 1, wherein said evaluation value generation means generates as the evaluation value a value determined by a downwardly convex function with respect to each of a first argument number which is the number of objects satisfying the classification condition in the first group and a second argument number which is the number of objects satisfying the classification condition in the second group, said apparatus further comprising:

upper limit estimation means of generating, as an upper limit value of the evaluation value in a possible region for the first argument number and the second argument number when one of the constituents is added to the first pattern and/or the second pattern, the maximum of values of the evaluation function at a plurality of end points of the region; and constituent addition means of performing processing for adding the same constituent to each of the first pattern and the second pattern or processing for adding the constituent to the second pattern when the measure indicated by the upper limit value is higher than the reference measure, and wherein said evaluation value generation means further generates the evaluation value with respect to the first pattern and/or the second pattern to which one of the constituents has been added by said constituent addition means.

3. The classification factor detection apparatus according to claim 2, wherein if the number of objects including the first pattern in the plurality of objects classified into the first group is a; the number of objects including the second pattern in the objects classified into the first group is b; the number of objects including the first pattern in the plurality of objects classified into the second group is c; and the number of objects including the second pattern in the objects classified into the second group is d, said evaluation value generation means generates, as the evaluation value, a value determined by f (a–c, b–d) which is the evaluation function generating the chi-square test value on the basis of (a–c) which is the first argument number and (b–d) which is the second arguments number; and said upper limit value estimation means generates, as an upper limit value of the chi-square test value when one of the constituents is added to each of the first pattern and the second pattern or to the second pattern, the maximum of f (a–c, b) which is the chi-square test value in the case where the number of objects including the second pattern in the second group is 0 and f(a, b–d) which is the chi-square test value in the case where the number of objects including the first pattern in the second group is 0.

4. The classification factor detection apparatus according to claim 2, wherein said upper limit value estimation means generates an upper limit value of the evaluation value in the case of adding the same constituent to each of the first pattern and the second pattern and in the case of adding the constituent to the second pattern while maintaining the same contents of the first pattern each time the evaluation value is generated by said evaluation value generation means;

when the measure indicated by the upper limit value is higher than the reference measure, said constituent addition means performs first addition processing for generating each of constituent-added second patterns formed by adding to the second pattern unevaluated constituents which are constituents not included in the second pattern in the plurality of constituents in one of the plurality of objects, and, if the first pattern and the second pattern are identical to each other, performs second addition processing for generating each of constituent-added first patterns and constituent-added second patterns formed by adding the unevaluated constituents to the first pattern and the second pattern; and said evaluation value generation means generates the evaluation value with respect to the constituent-added first pattern and constituent-added second pattern after the first or second addition processing.

5. The classification factor detection apparatus according to claim 2, further comprising:
   reference measure storage means of storing the reference measure; and
   reference measure updating means of storing, as the reference measure, in the reference measure storage means, the measure indicated by the evaluation value generated by said evaluation value generation means by relating the measure to the first pattern and the second pattern at the time of generation of the evaluation value if the measure indicated by the evaluation value exceeds the reference value,
   wherein said classification factor output means outputs, as a factor of classification, the first pattern and the second pattern stored in said reference measure storage means.

6. The classification factor detection apparatus according to claim 2, wherein said classification factor output means outputs, as a factor of classification, a classification condition corresponding to each of a predetermined number of evaluation values determined in advance in descending order of measure in a plurality of the evaluation values generated by said evaluation value generation means and indicating measures exceeding the reference measure.

7. The classification factor detection apparatus according to claim 1, wherein said evaluation value generation means generates as the evaluation value a value determined by an evaluation function which determines a value with respect to each of a first argument number which is the number of objects satisfying the classification condition in the first group and a second argument number which is the number of objects satisfying the classification condition in the second group, and the maximum of which corresponds to one of end points in a possible region for the first argument number and the second argument number, said apparatus further comprising:
   upper limit estimation means of generating, as an upper limit value of the evaluation value in a possible region for the first argument number and the second argument number when one of the constituents is added to the first pattern and/or the second pattern, the maximum of values of the evaluation function at a plurality of end points of the region; and
   constituent addition means of performing processing for adding the same constituent to each of the first pattern and the second pattern or processing for adding the constituent to the second pattern when the measure indicated by the upper limit value is higher than the reference measure, and
   wherein said evaluation value generation means further generates the evaluation value with respect to the first pattern and/or the second pattern to which one of the constituents has been added by said constituent addition means.

8. The classification factor detection apparatus according to claim 1, wherein the objects are sentences each formed of a plurality of words and/or phrases;
   a plurality of the sentences are classified into two groups according to genres indicating the contents of the sentences;
   said first selection means selects as the first pattern a set of at least one word or phrase in the words and phrases in one of the plurality of sentences;
   said second selection means selects as the second pattern a set of words and/or phrases formed by adding at least one word or phase to the first pattern;
   said evaluation value generation means generates the evaluation value according to the number of sentences satisfying the classification condition in the plurality of words and phrases classified into the first group and the number of sentences satisfying the classification condition in the sentences classified into the second group; and
   when the measure indicated by the evaluation value exceeds the reference measure, said classification factor output means outputs the set of words and/or phases in each of the first pattern and the second pattern and second pattern as a factor of classification of the plurality of sentences into the predetermined genres.

9. A classification factor detection method in which, with respect to the results of classification into two groups of a plurality of objects each constituted by a plurality of constituents through analysis as to whether or not each object has a predetermined characteristic, a set of some of the constituents is detected as a factor of the classification by a computer, said method comprising as steps performed by the computer:
   a first selection step of selecting a first pattern which is a set of at least one of the plurality of constituents of one of the plurality of objects;
   a second selection step of selecting, from the plurality of constituents in one of the plurality of objects, a second pattern formed of the first pattern and at least one of the constituents added to the first pattern;
   an evaluation value generation step of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, wherein the evaluation value is a chi-square test value representing the deviation of a probability distribution of the objects satisfying the classification condition based on the first pattern and the second pattern from a probability distribution of the objects satisfying a classification condition of a correlation equal to or lower than a predetermined value with the classification results; and
   a classification factor output step of outputting the constituents in each of the first pattern and the second pattern as a factor of classification when the measure indicated by the evaluation value exceeds a reference measure determined in advance.

10. The classification factor detection method according to claim 9, wherein, in said evaluation value generation step, the computer generates as the evaluation value a value determined by a downwardly convex function with respect to each of a first argument number which is the number of objects satisfying the classification condition in the first group and a second argument number which is the number of objects satisfying the classification condition in the second group, said method further comprising as steps performed by the computer:
   an upper limit estimation step of generating, as an upper limit value of the evaluation value in a possible region for the first argument number and the second argument number when one of the constituents is added to the first pattern and/or the second pattern, the maximum of values of the evaluation function at a plurality of end points of the region; and
   a constituent addition step of performing processing for adding the same constituent to each of the first pattern and the second pattern or processing for adding the constituent to the second pattern when the measure indicated by the upper limit value is higher than the reference measure, and wherein, in said evaluation value generation step, the computer further generates the evaluation value with respect to the first pattern and/or the second pattern to which one of the constituents has been added in said constituent addition step.

11. A computer program product comprising a tangible storage medium readable by a processing circuit and storing instructions for execution by the processing circuit for performing a classification factor detection method for detecting through analysis, with respect to results of classification into two groups of a plurality of objects, where each of said groups is constituted by a plurality of constituents, as to whether or not each object of the groups of objects has a predetermined characteristic, a set of some of the constituents as a factor of the classification, said method comprising the steps of:

of selecting a first pattern which first pattern is a set of at least one of the plurality of constituents of one of the plurality of objects;

selecting, from the plurality of constituents in one of the plurality of objects, a second pattern formed of the first pattern and at least one of the constituents added to the first pattern;

means of generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, wherein the evaluation value is a chi-square test value representing the deviation of a probability distribution of the objects satisfying the classification condition based on the first pattern and the second pattern from a probability distribution of the objects satisfying a classification condition of a correlation equal to or lower than a predetermined value with the classification results; and outputting the constituents in each of the first pattern and the second pattern as a factor of classification when the measure indicated by the evaluation value exceeds a reference measure determined in advance.

12. The computer program product according to claim 11, wherein said step of generating an evaluation value generates the evaluation value by determining a downwardly convex function with respect to each of a first argument number which is the number of objects satisfying the classification condition in the first group, and a second argument number which is the number of objects satisfying the classification condition in the second group, said method further including the steps of:

generating, as an upper limit value of the evaluation value in a possible region for the first argument number and the second argument number when one of the constituents is added to the first pattern and/or the second pattern, wherein maximum of values of the evaluation function at a plurality of end points of the region; and processing for adding the same constituent to each of the first pattern and the second pattern, or, processing for adding the constituent to the second pattern when the measure indicated by the upper limit value is higher than the reference measure.

13. A program storage device readable by machine, tangibly embodying a program of instructions executable by the machine to perform method steps for classification factor detection, said method steps comprising the steps of:

selecting a first pattern which is a set of at least one of the plurality of constituents of one of the plurality of objects;

selecting, from the plurality of constituents in one of the plurality of objects, a second pattern formed of the first pattern and at least one of the constituents added to the first pattern;

generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, wherein the evaluation value is a chi-square test value representing the deviation of a probability distribution of the objects satisfying the classification condition based on the first pattern and the second pattern from a probability distribution of the objects satisfying a classification condition of a correlation equal to or lower than a predetermined value with the classification results; and outputting the constituents in each of the first pattern and the second pattern as a factor of classification when the measure indicated by the evaluation value exceeds a reference measure determined in advance.

14. A computer program product comprising:

a computer-usable medium readable by a processing circuit and storing instructions for execution by the processing circuit for performing a classification factor detection method for analyzing, detecting and classifying objects into two groups of a plurality of objects, each of the two groups constituted by a plurality of constituents, based on whether or not each object has a predetermined characteristic, including using a set of some of the constituents as a factor of the classification, the classification factor detection method comprising the steps of:

selecting a first pattern which is a set of at least one of the plurality of constituents of one of the plurality of objects;

selecting, from the plurality of constituents in one of the plurality of objects, a second pattern formed of the first pattern and at least one of the constituents added to the first pattern;

generating an evaluation value for a measure of classification of the plurality of objects under a classification condition including the first pattern but not including the second pattern on the basis of the number of objects satisfying the classification condition in the plurality of objects classified into the first group and the number of objects satisfying the classification condition in the objects classified into the second group, wherein the evaluation value is a chi-square test value representing the deviation of a probability distribution of the objects satisfying the classification condition based on the first pattern and the second pattern from a probability distribution of the objects satisfying a classification condition of a correlation equal to or lower than a predetermined value with the classification results; and outputting the constituents in each of the first pattern and the second pattern as a factor of classification when the measure indicated by the evaluation value exceeds a reference measure determined in advance.

* * * * *